United States Patent
Stevens et al.

(10) Patent No.: US 7,261,720 B2
(45) Date of Patent: Aug. 28, 2007

(54) INFLATABLE DEVICE FOR USE IN SURGICAL PROTOCOL RELATING TO FIXATION OF BONE

(75) Inventors: Sheila S Stevens, Santa Clara, CA (US); Ryan P Boucher, San Francisco, CA (US); Lulu Follmer, Santa Clara, CA (US); Nenita Salom, Tracy, CA (US); Paul Reiss, Bernardsville, CA (US); Cesar Ico, San Francisco, CA (US); Karen D Talmadge, Palo Alto, CA (US); Mark A Reiley, Piedmont, CA (US); Arie Scholten, Manteca, CA (US)

(73) Assignee: Kyphon Inc., Sunnyvale, CA (US)

( * ) Notice: Subject to any disclaimer, the term of this patent is extended or adjusted under 35 U.S.C. 154(b) by 89 days.

(21) Appl. No.: 10/265,922

(22) Filed: Oct. 7, 2002

(65) Prior Publication Data

US 2004/0092948 A1  May 13, 2004

Related U.S. Application Data

(63) Continuation-in-part of application No. 10/044,843, filed on Jan. 11, 2002, now abandoned.

(51) Int. Cl.
*A61B 17/66* (2006.01)

(52) U.S. Cl. .................. 606/105; 606/90; 606/191; 606/192

(58) Field of Classification Search .............. 606/90, 606/105, 191, 192; 600/37, 207, 201, 206, 600/208, 235; 601/151, 152, 153; 604/101.05, 604/103.09
See application file for complete search history.

(56) References Cited

U.S. PATENT DOCUMENTS

| 2,849,002 A | 8/1958 | Oddo |
| 3,045,677 A | 7/1962 | Wallace |

(Continued)

FOREIGN PATENT DOCUMENTS

| EP | 0 274 411 | 9/1988 |

(Continued)

*Primary Examiner*—Cris Rodriguez
*Assistant Examiner*—Candice C. Stokes
(74) *Attorney, Agent, or Firm*—Ryan Kromholz & Manion, S.C.

(57) ABSTRACT

A balloon for use in compressing cancellous bone and marrow (also known as medullary bone or trabecular bone). The balloon comprises an inflatable balloon body for insertion into said bone. The body has a shape and size to compress at least a portion of the cancellous bone to form a cavity in the cancellous bone and/or to restore the original position of the outer cortical bone, if fractured or collapsed. The balloon desirably incorporates restraints which inhibit the balloon from applying excessive pressure to various regions of the cortical bone. The wall or walls of the balloon are such that proper inflation of the balloon body is achieved to provide for optimum compression of the bone marrow. The balloon can be inserted quickly into a bone. The balloon can be made to have a suction catheter. The balloon can be used to form and/or enlarge a cavity or passage in a bone, especially in, but not limited to, vertebral bodies. Various additional embodiments facilitate directionally biasing the inflation of the balloon.

13 Claims, 21 Drawing Sheets

U.S. PATENT DOCUMENTS

| | | | |
|---|---|---|---|
| 3,154,077 A | 10/1964 | Cannon | |
| 3,640,282 A | 2/1972 | Kamen et al. | |
| 3,648,294 A | 3/1972 | Shahrestani | |
| 3,779,239 A | 12/1973 | Fischer et al. | |
| 3,779,241 A * | 12/1973 | Vennard et al. | 128/836 |
| 3,850,176 A | 11/1974 | Gottschalk | |
| 3,889,685 A | 6/1975 | Miller, Jr. et al. | |
| 4,261,339 A | 4/1981 | Hanson et al. | |
| 4,292,974 A | 10/1981 | Fogarty et al. | |
| 4,327,736 A | 5/1982 | Inoue | |
| 4,338,942 A | 7/1982 | Fogarty | |
| 4,402,307 A | 9/1983 | Hanson et al. | |
| 4,467,790 A | 8/1984 | Schiff | |
| 4,531,512 A | 7/1985 | Wolvek et al. | |
| 4,753,238 A * | 6/1988 | Gaiser | 606/195 |
| 4,796,629 A * | 1/1989 | Grayzel | 606/194 |
| 4,848,344 A | 7/1989 | Sos et al. | |
| 4,917,088 A | 4/1990 | Crittenden | |
| 4,969,888 A | 11/1990 | Scholten et al. | |
| 4,983,167 A | 1/1991 | Sahota | |
| 5,102,390 A | 4/1992 | Crittenden et al. | |
| 5,104,376 A | 4/1992 | Crittenden | |
| 5,108,404 A | 4/1992 | Scholten et al. | |
| 5,163,989 A | 11/1992 | Campbell et al. | |
| 5,295,994 A | 3/1994 | Bonutti | |
| 5,352,199 A | 10/1994 | Tower | |
| 5,415,635 A | 5/1995 | Bagaoisan et al. | |
| 5,500,181 A | 3/1996 | Wang et al. | |
| 5,514,153 A | 5/1996 | Bonutti | |
| 5,587,125 A | 12/1996 | Roychowdhury | |
| 5,741,282 A | 4/1998 | Anspach, III et al. | |
| 5,766,151 A | 6/1998 | Valley et al. | |
| 5,827,289 A | 10/1998 | Reiley et al. | |
| 5,843,116 A | 12/1998 | Crocker et al. | |
| 5,938,582 A | 8/1999 | Ciamacco, Jr. et al. | |
| 5,972,015 A | 10/1999 | Scribner et al. | |
| 6,048,346 A | 4/2000 | Reiley et al. | |
| 6,066,154 A | 5/2000 | Reiley et al. | |
| D439,980 S | 4/2001 | Reiley et al. | |
| 6,235,043 B1 | 5/2001 | Reiley et al. | |
| 6,241,734 B1 | 6/2001 | Scribner et al. | |
| 6,248,110 B1 | 6/2001 | Reiley et al. | |
| 6,379,373 B1 | 4/2002 | Sawhney et al. | |
| 6,383,212 B2 | 5/2002 | Durcan et al. | |
| 6,607,544 B1 | 8/2003 | Boucher et al. | |
| 6,663,647 B2 | 12/2003 | Reiley et al. | |
| 6,863,672 B2 | 3/2005 | Reiley et al. | |

FOREIGN PATENT DOCUMENTS

| | | |
|---|---|---|
| EP | 0 597 465 | 9/1988 |
| EP | 0 135 990 | 9/1990 |
| EP | 0 410 072 | 1/1991 |
| EP | 0 436 501 | 4/1993 |
| EP | 0 420 488 | 7/1993 |
| EP | 0 439 202 | 9/1993 |
| EP | 0 592 885 | 9/1993 |
| EP | 0 318 919 | 1/1994 |
| EP | 0 383 794 | 6/1994 |
| EP | 0 355 937 | 11/1995 |
| EP | 0 713 712 | 5/1996 |
| EP | 0 730 879 | 9/1996 |
| EP | 0 531 117 | 1/1997 |
| EP | 0 362 826 | 5/1997 |
| EP | 0 566 684 | 6/1997 |
| EP | 0 779 062 | 6/1997 |
| EP | 0 826 395 | 3/1998 |
| EP | 0 834 293 | 4/1998 |
| WO | WO89/02763 | 4/1989 |
| WO | WO91/17788 | 11/1991 |
| WO | WO92/11892 | 7/1992 |
| WO | WO92/19440 | 11/1992 |
| WO | WO94/02197 | 2/1994 |
| WO | WO95/20362 | 8/1995 |
| WO | WO 95/20362 | 8/1995 |
| WO | WO95/22367 | 8/1995 |
| WO | WO96/04951 | 2/1996 |
| WO | WO96/12516 | 5/1996 |
| WO | WO96/39970 | 12/1996 |
| WO | WO97/03716 | 2/1997 |
| WO | WO97/17098 | 5/1997 |
| WO | WO97/17099 | 5/1997 |
| WO | WO97/40877 | 11/1997 |
| WO | WO98/03218 | 1/1998 |
| WO | WO 98/56301 | 12/1998 |
| WO | WO98/56301 | 12/1998 |
| WO | WO99/29246 | 6/1999 |
| WO | WO99/37212 | 7/1999 |
| WO | WO99/51149 | 10/1999 |
| WO | WO 99/62416 | 12/1999 |
| WO | WO99/62416 | 12/1999 |
| WO | WO 01/28439 | 4/2001 |
| WO | WO 01/76514 | 10/2001 |
| WO | WO 02/30338 | 4/2002 |

* cited by examiner

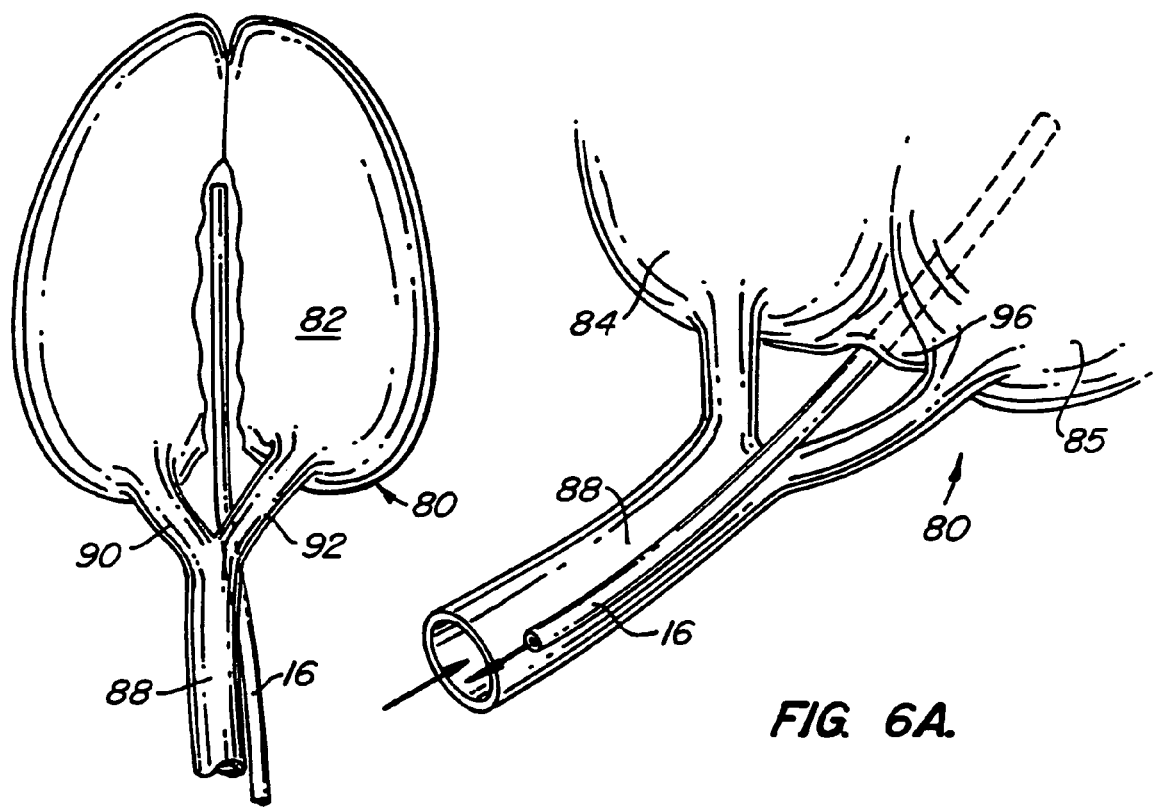
FIG. 6.
FIG. 6A.
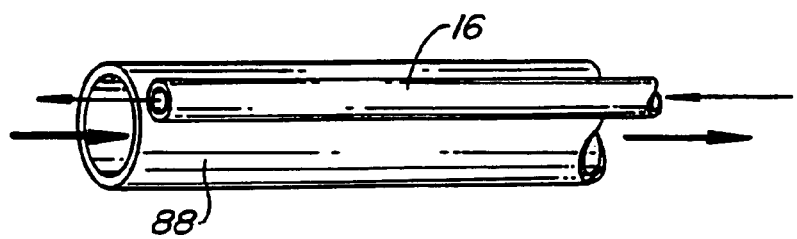
FIG. 7.
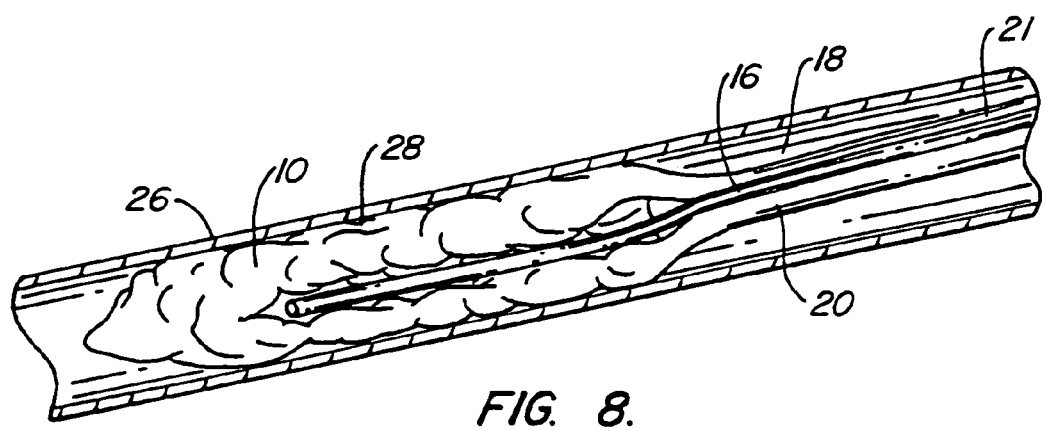
FIG. 8.

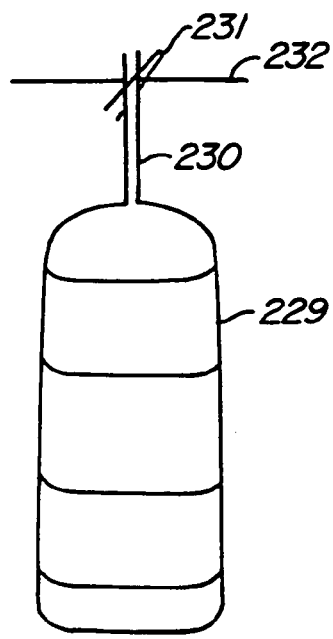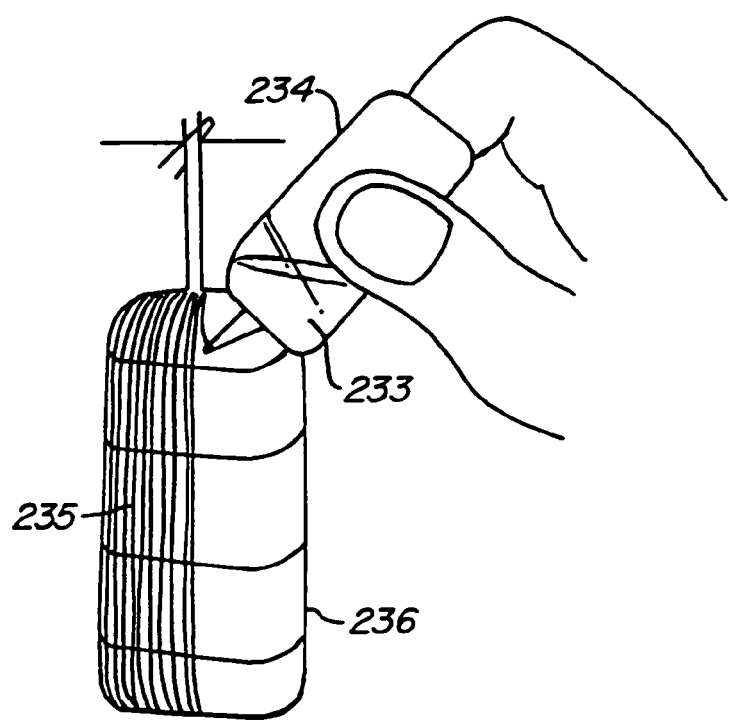
FIG. 22A.  FIG. 22B.
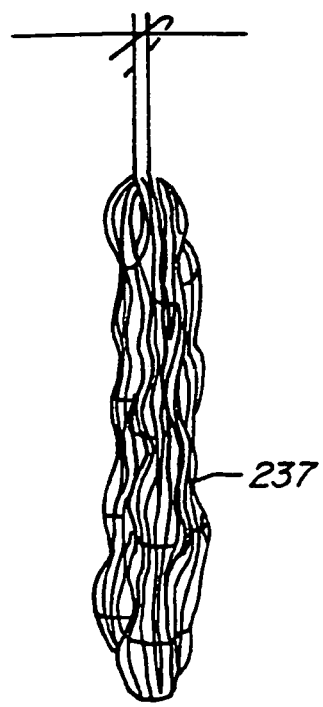
FIG. 22C.

INFLATABLE DEVICE FOR USE IN SURGICAL PROTOCOL RELATING TO FIXATION OF BONE

This application is a continuation-in-part of application Ser. No. 10/044,843, filed Jan. 11, 2002, now abandoned, which claims the benefit of application Ser. No. 10/054,736 filed Oct. 24, 2001, both entitled "Devices and Methods using an Expandable Body with Internal Restraints for Compressing Cancellous Bone".

FIELD OF THE INVENTION

This invention relates to the treatment of bone conditions in human and other animals.

BACKGROUND OF THE INVENTION

When cancellous bone becomes diseased, for example, because of osteoporosis, avascular necrosis, or cancer, the surrounding cortical bone becomes more prone to compression fracture or collapse. This is at least in part because the cancellous bone no longer provides interior support for the surrounding cortical bone. The bone disease may also affect the strength and integrity of the surrounding cortical bone, further disposing the bone to fracture and/or collapse.

There are 2 million fractures each year in the United States, of which about 1.3 million are caused by osteoporosis alone. There are also other bone diseases involving infected bone, poorly healing bone, or bone fractured by severe trauma. Moreover, the use of various drugs, such as steroids, tobacco and/or the excessive intake of alcohol, can significantly degrade bone quality. Any of these conditions, if not successfully addressed, can result in fracture and/or collapse of bone, causing deformities, chronic complications, and an overall adverse impact upon the quality of life.

U.S. Pat. Nos. 4,969,888 and 5,108,404 disclose apparatus and methods for the fixation of fractures or other conditions of human and other animal bone systems, both osteoporotic and non-osteoporotic. Among other inventions, these patents disclose devices and methods that employ an expandable body to compress cancellous bone and/or create an interior cavity within the targeted bone. The cavity receives a filling material, which hardens and provides renewed interior structural support for cortical bone.

The better and more efficacious treatment of bone disease that these patents promise can be more fully realized with improved systems and methods for making and deploying expandable bodies in bone.

SUMMARY OF THE INVENTION

The present invention is directed to a balloon that can be used to treat bones predisposed to fracture or collapse. These balloons comprise one or more inflatable balloon bodies for insertion into said bone. The body has a preferred shape and size when substantially inflated sufficient to compress at least a portion of the inner cancellous bone to create a cavity in the cancellous bone and/or to restore the original position of the outer cortical bone, if fractured or collapsed. In various embodiments, the balloon body is restrained to create said preferred shape and size so that the fully inflated balloon body is desirably inhibited from applying substantial pressure to a single point on the inner surface of the outer cortical bone if said bone is unfractured or uncollapsed.

In addition to the shape of the inflatable device itself, another important aspect is the construction of the wall or walls of the balloon such that the proper inflation of the balloon body is achieved to provide for optimum compression of the cancellous bone. The material of the balloon is also desirably chosen so the balloon can be inserted quickly and easily into a bone through a cannula, yet can also withstand high pressures when inflated. For example, the material could be chosen to facilitate folding of the balloon. Alternatively, the material could desirably allow plastic, elastic and/or semi-elastic deformation of the balloon during inflation. The material will also desirably resist abrasion and/or puncture of the balloon when in contact with cortical and/or cancellous bone during introduction and inflation of the balloon. The balloon can also include optional ridges or indentations which are imparted to the cavity, desirably remaining in the cavity walls after the balloon has been removed, to enhance the stability of the bone void filler. Also, the inflatable device can be made to have an optional, built-in suction catheter. This may be used to remove any fat or fluid extruded from the bone during balloon inflation in the bone. Also, the balloon body can be protected from puncture (by the surrounding bone or cannula) by being covered while inside the cannula and/or bone with an optional protective sleeve of suitable materials, such as Kevlar® fiber products or polyethylene tetraphthalate (PET) or other polymer or substance that can protect the balloon. This covering material may also provide the additional advantage of reducing friction between the balloon and cannula, or it can incorporate a lubricating material, such as silicone, to reduce friction. One important purpose of the inflatable device, therefore, is the forming or enlarging of a cavity or passage in a bone, especially in, but not limited to, vertebral bodies.

In one aspect, the invention provides an improved balloon-like inflatable device for use in carrying out a surgical protocol of cavity formation in bones to enhance the efficiency of the protocol, to minimize the time required to performing the surgery for which the protocol is designed, and to improve the clinical outcome. If desired, these balloons may approximate the inner shape of the bone they are inside of in order to maximally compress cancellous bone. They may also have additional design elements to achieve specific clinical goals. In various embodiments, they are made of inelastic, semi-elastic, elastomeric or plastically deformable materials and kept in their defined configurations when inflated by various restraints, including, but not limited to, use of inelastic, semi-elastic, elastomeric or plastically deformable materials in conjunction with the balloon body, seams in the balloon body created by bonding or fusing separate pieces of material together or by fusing or bonding together opposing sides of the balloon body, woven material bonded inside or outside the balloon body, strings or bands placed at selected points in the balloon body, and stacking balloons of similar or different sizes or shapes on top of each other by gluing or by heat fusing them together. Optional ridges or indentations created by the foregoing structures, or added on by bonding additional material, can increase stability of the bone void filler. The ridges or indentations may also help keep the bone filler material in a desired position during subsequent loading and/or healing of the treated bone. Optional suction devices, preferably placed so that at least one such device is located approximate the lowest point of the cavity being formed, will desirably allow the cavity to be cleaned and/or permit fluid or solids to be removed from and/or introduced into the cavity before filling.

Among the various embodiments of the present invention are the following:

1. A doughnut (or torus) shaped balloon with an optional built-in suction catheter to remove fat and other products extruded during balloon expansion.

2. A balloon with a spherical outer shape surrounded by a ring-shaped balloon segment for body cavity formation.

3. A balloon which is kidney bean shaped in configuration. Such a balloon can be constructed in a single layer, or several layers stacked on top of each other. This embodiment can also be a square or a rectangle instead of a kidney bean.

4. A spherically shaped balloon approximating the size of the head of the femur (i.e. the proximal femoral epiphysis). Such a balloon can also be a hemisphere.

5. A balloon in the shape of a humpbacked banana or a modified pyramid shape approximating the configuration of the distal end of the radius (i.e. the distal radial epiphysis and metaphysis).

6. A balloon in the shape of a cylindrical ellipse to approximate the configuration of either the medial half or the lateral half of the proximal tibial epiphysis. Such a balloon can also be constructed to approximate the configuration of both halves of the proximal tibial epiphysis.

7. A balloon in the shape of a sphere on a base to approximate the shape of the proximal humeral epiphysis and metaphysis with a plug to compress cancellous bone into the diaphysis, sealing it off. Such an embodiment can also be a cylinder.

8. A balloon in the shape of a boomerang to approximate the inside of the femoral head, neck and lesser trochanter, allowing a procedure to prevent hip fracture.

9. A balloon in the shape of a cylinder to approximate the size and shape of the inside of the proximal humerus or of the distal radius.

10. A balloon in the shape of a peanut or hourglass with an internal membrane to constrain expansion preferentially along one or more axes.

11. A balloon in the shape of a disk.

12. A balloon having multiple inflatable sections or lobes that can be individually inflated and/or deflated.

13. A balloon device with an optional suction device.

14. Protective sheaths to act as puncture guard members optionally covering each balloon inside its catheter.

The present invention, therefore, provides improved, inflatable devices for creating or enlarging a cavity or passage in a bone wherein the devices are inserted into the bone. In various embodiments, the configuration of each device can be defined by the surrounding cortical bone and adjacent internal structures, and is designed to occupy up to 70-90% of the volume of the inside of the bone, although balloons that are as small as about 40% (or less) and as large as about 99% are workable for fractures. In various other embodiments, the inflated balloon size may be as small as 10% of the cancellous bone volume of the area of bone being treated, such as for the treatment of avascular necrosis and/or cancer, due to the localized nature of the fracture, collapse and/or treatment area. The fully expanded size and shape of the balloon is desirably regulated by material in selected portions of the balloon body whose resistance to expansion creates a restraint as well as by either internal or external restraints formed in the device including, but not limited to, mesh work, webbing, membranes, partitions or baffles, a winding, spooling or other material laminated to portions of the balloon body, continuous or non-continuous strings across the interior of the balloon held in place at specific locations by bonding to the inside of the balloon (by glue, welding, etc.) or by threading these strings through to the outside, and seams in the balloon body created by bonding two pieces of body together or by bonding opposing sides of a body through glue or heat. Aside from the use of different materials, the objectives of the present invention could similarly be accomplished by utilizing different thicknesses of materials to regulate the expansion of the balloon body. Moreover, the use of similar materials of differing elasticity, for example a polyurethane plastic balloon (incorporating cross-linking agents) having discrete sections that are cross-linked by gamma radiation exposure and which are thus less prone to expansion, could accomplish the objectives of the present invention as well.

Spherical portions of balloons may be restrained by using inelastic, semi-elastic, elastic and elastomeric materials in the construction of the balloon body, or may be additionally restrained as just described. The material of the balloon can be a non-elastic material, such as polyethylene tetraphthalate (PET), nylon, Kevlar® or other patented or nonpatented medical balloon materials. It can also be made of semi-elastic materials, such as silicone, rubber, thermoplastic rubbers and elastomers or elastic materials such as latex or polyurethane, if appropriate restraints are incorporated. The restraints can be continuous or made of discrete elements of a flexible, inelastic high tensile strength material including, but not limited to, the materials described in U.S. Pat. No. 4,706,670, which is incorporated herein by reference. The thickness of the balloon wall is typically in the range of 2/1000ths to 25/1000ths of an inch, although other thicknesses that can withstand increased pressures, such as 250-400 psi or greater, even up to 500, 1000 or 2000 psi, may be used.

One important goal of percutaneous vertebral body augmentation and of the present invention is to provide a balloon which can create a cavity inside the vertebral body whose configuration is optimal for supporting the bone. Another important goal is to move the top and bottom of the vertebral body (otherwise known as the upper and lower endplates) toward a more normal anatomical position to restore height where possible. Both of these objectives, however, are desirably achieved without significantly altering the outer dimensions of the sides of the vertebral body, either by fracturing the cortical sidewalls of the vertebral body or by moving already fractured bone in the sidewalls.

The present invention satisfies these goals through the design of inflatable devices to be described. Inflating such a device desirably creates a cavity within the calcium-containing soft cancellous bone (such as by compressing the cancellous bone) and/or desirably displaces surrounding cortical bone towards a more normal anatomical position.

In one embodiment, the balloon body desirably recreates the shape of the inside of an unfractured vertebral body, and optimally grows no more than a maximum of 70 to 90% of the inner volume. The balloons of these embodiments are designed such that maximally inflating them will desirably recreate the predetermined shape and size. However, conventional balloons become spherical when inflated. Spherical shapes do not typically permit the hardened bone void filler to support the spine adequately, because they can create a generally spherical cavity which, when filled with filler material, makes single points of contact on the vertebral body surfaces (the equivalent of a circle inside a square, or a sphere inside a cylinder). In contrast, various embodiments of the balloons of the present invention more generally recreate the flat surfaces of the vertebral body by incorporating restraints that maintain the balloon in desired shapes. These desired shapes create cavities which, when filled with filler material, desirably distribute the load transferred from the vertebral body surfaces to the bone void fillers, which ultimately strengthens the spine. In addition, the volume of bone void filler that fills these cavities desirably creates a thick mantle of cement (for example a thickness of 4 mm or greater), which increases the compressive strength of the filler material. Another useful feature of various embodiments is the incorporation of ridges in the balloons which can leave one or more imprints in the walls of the cavity created within the compressed cancellous bone. The resulting bone void filler "fingers," which will ultimately fill these imprints, can provide enhanced stability, and reduce the opportunity for the filler material to shift or displace within the vertebral body under compressive loading of the spine.

Balloons which can optimally compress cancellous bone in vertebral bodies include the balloons listed as balloon types 1-3, 10, 12 and 13 above. Some of these balloons are desirably configured to approximate the shape of the vertebral body. Since the balloon can be chosen to occupy less than the total inner volume (prior to fracture) of the targeted vertebral body, inflation of the balloon will desirably not exert undue pressure on the surrounding cortical sidewalls of the vertebral body (the sidewalls of the vertebral body will desirably not expand beyond their existing size—either fractured or unfractured). However, since the upper and lower end plates of the vertebral body are typically depressed in a compression fracture, and the balloon can be approximately the height of an unfractured vertebral body, inflation of the balloon can move the top and bottom end plates back towards their pre-fractured position and/or orientation. Moreover, a plurality of individual balloons can be utilized inside the vertebral body, such as by being stacked, and stacks containing any of the disclosed balloon types can be mixed in shape and/or size to provide greater flexibility and/or control.

A primary goal of percutaneous femoral (or humeral) head augmentation (balloon type 4), percutaneous distal radius augmentation (balloon type 5), percutaneous proximal tibial augmentation (balloon type 6), and percutaneous proximal humeral augmentation (balloon type 7) is to create a cavity whose configuration is optimal to support the bone to be treated. Another important goal is to compress avascular (or aseptic) necrotic bone or to support avascular necrotic bone. Yet another important goal is to help realign the fracture fragments. These goals are generally achieved by exerting pressure primarily on the cancellous bone which may be transferred to the surrounding cortical bone. Pressure directly on a small section of the cortical bone could conceivably cause worsening of the fracture, which, while not precluded, is desirably avoided. The design of various embodiments of the inflatable devices approximates the shape of the bone to be treated. The approximate volume of the cavity made by the inflatable device(s) can be as much as 70 to 90% of the volume of the bone to be treated. In the case of avascular necrosis, depending upon the extent of the avascular necrosis, a smaller or larger cavity inside bone will be formed. In some cases, if the area of avascular necrosis is small, a small balloon will be utilized which might create a cavity only 10 to 15% of the total volume. If larger areas are involved with avascular necrosis, then one or more larger balloons could be utilized which might create a much larger cavity, including cavities as large as 80 to 90% of the volume of the bone (or greater). The present invention satisfies these goals through the design of the inflatable devices to be described.

For example, percutaneous hip augmentation (as shown in connection with balloon type 8) is designed to prevent and/or treat hip fracture by compacting weak cancellous bone in the femur where hip fractures occur and replacing it with an appropriate supporting material. The present invention satisfies this goal through the design of the inflatable devices to be described.

The present invention discloses improved systems for deployment in bone comprising structures adapted to assume expanded geometries having a desired configuration when used. These expandable structures include material that allows the structure to differentially expand when under internal pressure. These structures, when in use, are able to expand preferentially along one or more axes so as to deliver a greater force and/or displacement of cancellous bone towards one direction versus another. Furthermore, such structures, when distended, can generally match the geometry of the interior bone space in which the structure is deployed, if desired. For example, such structures could optimally expand to a desired shape rather than simply towards areas of lowest bone density, i.e. expansion of the structure is can be controlled even when encountering areas in the bone of varying resistance.

Moreover, the exposure of the expandable structure to cancellous bone also typically requires materials having significant resistance to surface abrasion, puncture and/or tensile stresses. For example, structures incorporating elastomer materials, e.g., polyurethane, which have been preformed to a desired shape, e.g., by exposure to heat and pressure, can undergo controlled expansion and further distention in cancellous bone, without failure, while exhibiting resistance to surface abrasion and puncture when contacting cancellous bone.

The present invention further discloses inflatable devices that have one or more biased directions of inflation. For example, inflatable devices having reduced lateral growth may provide improved fracture reduction because such devices can exert a greater vertical force and/or displacement within the treated bone. Such inflatable devices may also protect the lateral and anterior/posterior sidewalls of the vertebral body by minimizing expansion towards these sidewalls and directing expansion to a greater degree along the longitudinal axis of the spine. In situations where a surgical procedure is terminated when the inflatable device contacts a lateral cortical wall of the targeted bone, such biased expansion could permit improved fracture reduction prior to reaching this procedure endpoint.

The present invention further discloses inflatable devices having biased inflation along the longitudinal axis of the inflatable devices. Inflatable devices capable of biased inflation along their longitudinal axes may provide improved fracture reduction as such devices can be preferentially expanded towards areas of higher cancellous bone density and/or away from areas of lower cancellous bone density. Similarly, inflatable devices capable of biased inflation along their longitudinal axes can be preferentially expanded towards areas that resist expansion of the device and/or away from areas that promote expansion of the device.

Due to the nature of the injury, disease or other treatments, as well as the health and age of the patient suffering from these injuries, it may be preferable to treat a bone with the devices of this invention during an open or semi-open surgical procedure. In addition, a goal of the surgery may be to replace the diseased or injured bone with materials (such as bone fillers or certain drugs) which do not flow, and which thus are not well suited for a more minimally invasive procedure.

Features and advantages of the invention are set forth in the following Description and Drawings, as well as in the appended claims.

BRIEF DESCRIPTION OF THE DRAWINGS

FIG. 6 shows an oblong-shaped balloon with a catheter extending into the central portion of the balloon.

FIG. 6A is a perspective view of one way in which a catheter can be arranged relative to the inner tubes for inflating the balloon of FIG. 6.

FIG. 7 is a suction tube and a contrast injection tube for carrying out the inflation of the balloon and removal of debris caused by expansion from the balloon itself.

FIG. 8 is a vertical section through a balloon after it has been deflated and as it is being inserted into the vertebral body of a human.

FIGS. 22A-C are schematic illustrations of a representative method and system for delivering a therapeutic substance to a bone according to the present invention.

DETAILED DESCRIPTION OF THE PREFERRED EMBODIMENT

I. Balloons for Anatomical Structures

A. Balloons for Vertebral Bodies

A first embodiment of the balloon (FIG. 1) constructed in accordance with the teachings of the present invention is broadly denoted by the numeral 10 and includes a balloon body 11 having a pair of hollow, inflatable parts 12 and 14 comprised of flexible material, including (but not limited to) non-elastic materials such as PET, mylar or Kevlar®, elastic materials such as polyurethane, latex or rubber, semi-elastic materials such as silicone, or other materials. Parts 12 and 14 have a suction tube 16 therebetween for drawing fats and other debris by suction into tube 16 for transfer to a remote disposal location. Tube 16 has one or more suction holes so that suction may be applied to the open end of tube 16 from a suction source (not shown).

Figure 1:
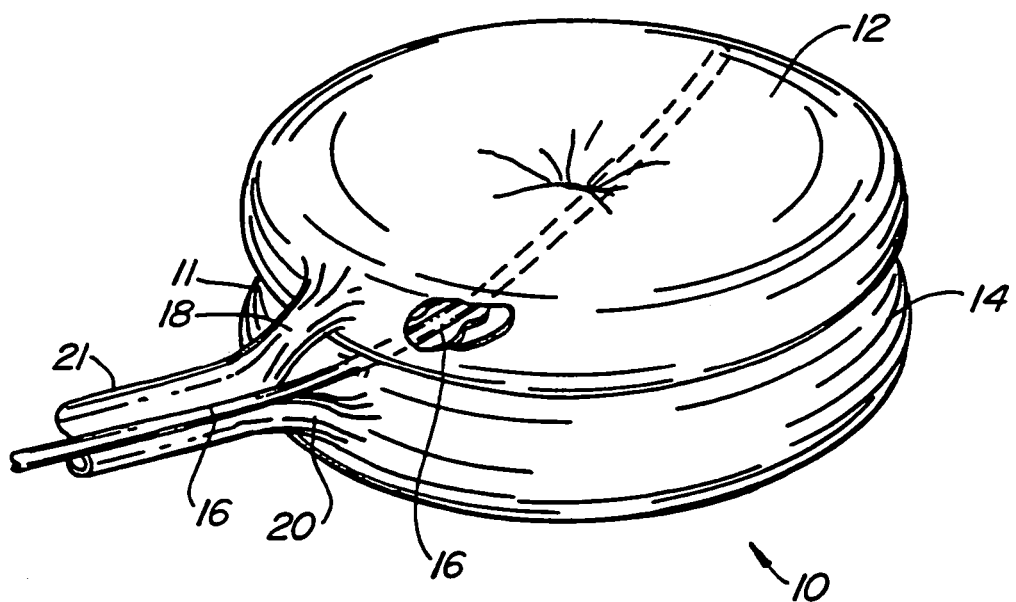
FIG. 1 is a perspective view of a first embodiment of a balloon constructed in accordance with the teachings of the present invention, the embodiment being in the shape of a stacked doughnut assembly.

In this embodiment, the parts 12 and 14 are connected together by an adhesive which can be of any suitable type for adhering such materials as well as by bonding, i.e. thermal bonding (laser, radio-frequency (RF)/induction, heated dies), ultrasonic welding, solvent bonding, etc. Parts 12 and 14 are doughnut-shaped as shown in FIG. 1 and have tubes 18 and 20 which communicate with and extend away from the parts 12 and 14, respectively, to a source of inflating fluid under pressure (not shown). The inflating fluid is preferably a liquid. The liquid inflates the balloon 10, particularly parts 12 and 14 thereof, after the balloon has been inserted in a collapsed condition (FIG. 8) into a bone to be treated, such as a vertebral bone 22 in FIG. 2. The previously-mentioned U.S. Pat. Nos. 4,969,888 and 5,108,404, the disclosures of which are incorporated herein by reference, disclose the use of a guide pin and cannula for inserting the balloon into bone to be treated when the balloon is deflated and has been inserted into the targeted bone where the balloon is inflated.

FIG. 8 shows a deflated balloon 10 being inserted through a cannula 26 into bone. The balloon in cannula 26 is deflated and is forced through the cannula by exerting manual force on the catheter 21 which extends into a passage 28 extending into the interior of the bone. The catheter is slightly flexible but is sufficiently rigid to allow the balloon to be forced into the interior of the bone where the balloon is then inflated by directing fluid into the tube 88 whose outlet ends are coupled to respective parts 12 and 14.

Figure 2:
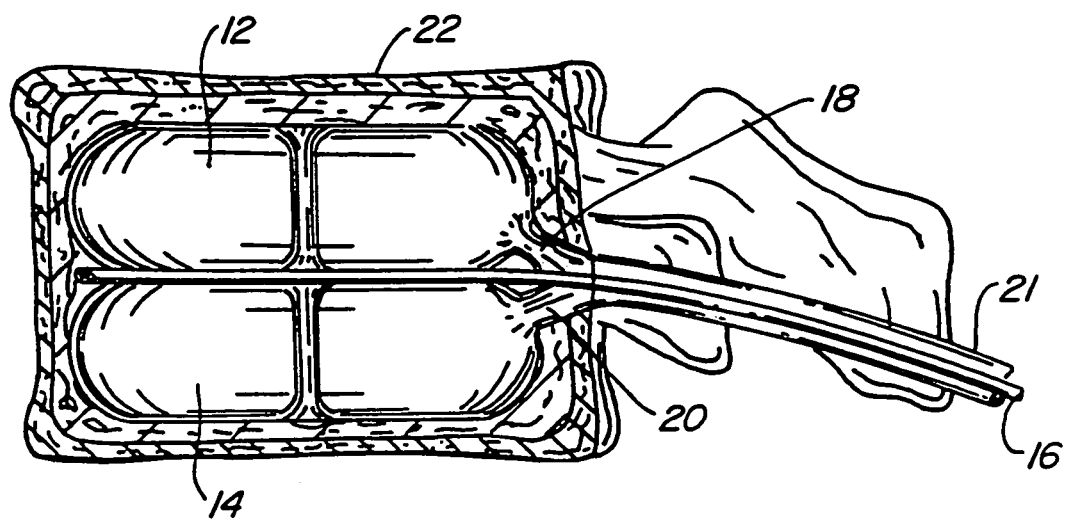
FIG. 2 is a vertical section through the balloon of FIG. 1 showing the way in which the doughnut portions of the balloon of FIG. 1 fit into a cavity of a vertebral body.

In use, the balloon 10 is initially deflated and, after the bone to be filled with the balloon has been prepared to receive the balloon (such as by punching, drilling or otherwise displacing a small amount of the cancellous bone directly beyond the opening of the cannula), the deflated balloon is advanced into the bone in a collapsed condition through the cannula 26. In this embodiment, the balloon is oriented preferably in the bone such that the balloon expansion permits minimal pressure to be exerted on the cortical bone if there were no fracture or collapse of the bone (FIG. 2). Where such fracture or collapse has not occurred, such pressure would desirably compress the bone marrow and/or cancellous bone against the inner wall of the cortical bone, thereby compacting the bone marrow of the bone to be treated and to further enlarge the cavity in which the bone marrow is to be replaced by a biocompatible, flowable bone material.

The balloon is inflated to compact the bone marrow and/or cancellous bone in the cavity and, after compaction of the bone marrow and/or cancellous bone, the balloon is deflated and removed from the cavity. While inflation of the balloon and compaction occurs, fats and other debris may be removed from the space between and around parts 12 and 14 by applying a suction force to catheter tube 16, if desired. Following this, and following the compaction of the bone marrow, the balloon is deflated and pulled out of the cavity by applying a manual pulling force to the catheter tube 21.

Figure 4:
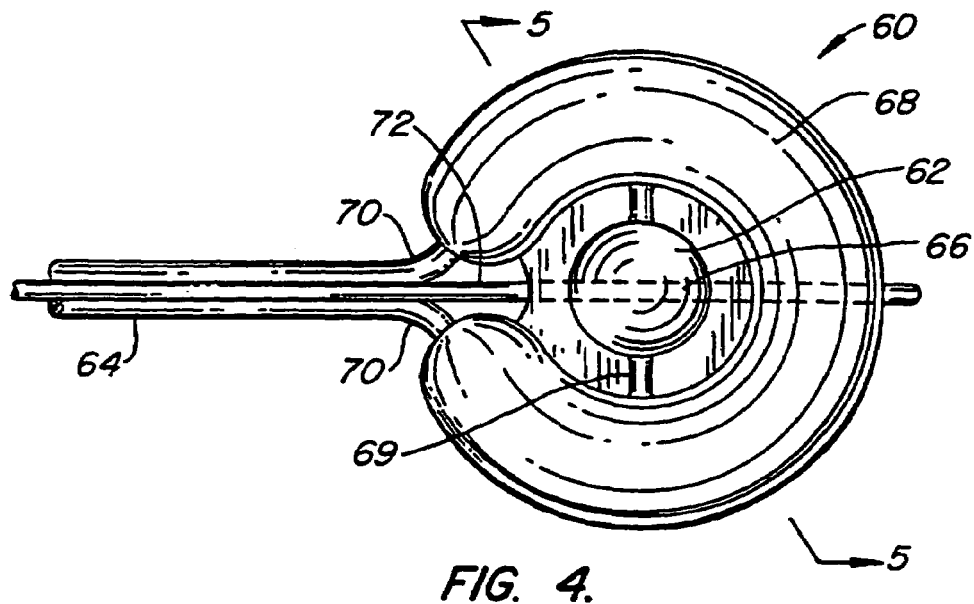
FIG. 4 is a top plan view of a spherical balloon having a cylindrical ring surrounding the balloon.
Figure 5:
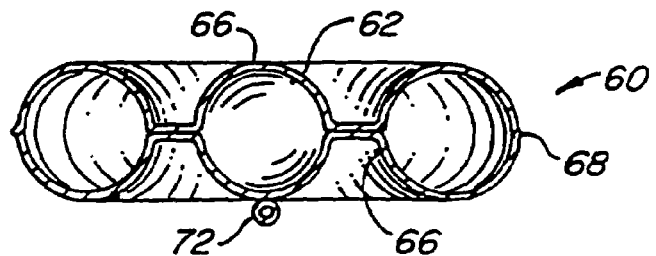
FIG. 5 is a vertical section through the spherical balloon and ring of FIG. 4.

Another embodiment of an inflatable device constructed in accordance with the teachings of the present invention is broadly denoted by the numeral 60 and is shown in FIGS. 4 and 5. The balloon 60 includes a central spherical part 62 which is hollow and which receives an inflating liquid under pressure through a tube 64. The spherical part is provided with a spherical outer surface 66 and has an outer periphery which is surrounded substantially by a ring shaped part 68 having tube segments 70 for inflation of part 68. A pair of passages 69 interconnect parts 62 and 68. A suction tube segment 72 draws liquid and debris from the bone cavity being formed by the balloon 60.

Figure 9:
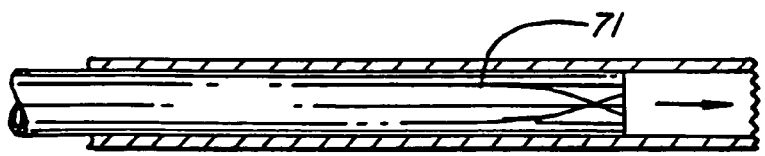
FIGS. 9 and 9A are side elevational view of a cannula showing how the protective sleeve or guard member can expand when leaving the cannula.
Figure 9B:
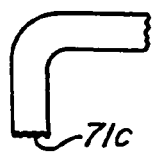
FIG. 9B is a vertical section through a vertebral bone into which an access hole has been drilled.
Figure 9A:
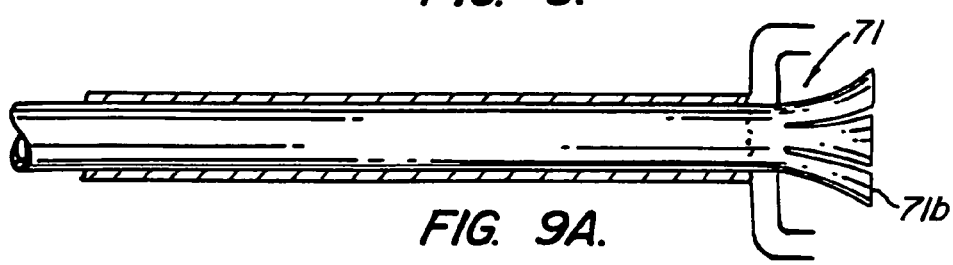

Provision can be made for a balloon sleeve 71 (FIG. 9) for the balloon 60 as well as for all balloons disclosed herein. A balloon sleeve 71 can be shiftably mounted in an outer tube 71a (such as a cannula) and can be used to insert the balloon 60 when deflated into a cortical bone. The sleeve 71 has resilient fingers 71b which bear against the interior of the entrance opening 71c of the vertebral bone 22 to prevent rearing or bunching of the balloon 60 and to guard against cortical bone shards which may remain near the entrance opening. Upon removal of the balloon sleeve (or, alternatively, the sleeve can remain in position within the bone), liquid under pressure will be directed into the tube 64 which will inflate parts 62 and 68 so as to compact the bone marrow within the cortical bone. Following this, the balloon 60 is deflated and removed from the bone cavity, at which time the sleeve 71 can optionally facilitate removal of the balloon.

FIGS. 6 and 6A show views of a modified balloon 80 of the type shown in FIGS. 1 and 2, with at least one difference being the individual inflated portions of the balloon 80 are not stitched onto one another. In FIG. 6, the balloon 80 has a pear-shaped outer convex surface 82 which is made up of a first hollow part 84 and a second hollow part 85. A tube 88 is provided for directing liquid into the two parts along branches 90 and 92 to inflate the parts after the parts have been inserted into the medullary cavity of a bone. A catheter tube 16 is inserted into the space 96 between two parts of the balloon 80. An adhesive bonds the two parts 84 and 85 together at the interface thereof.

FIG. 6A shows one way in which the catheter tube 16 is inserted into the space or opening 96 between the two parts of the balloon 80.

FIG. 7 shows the tube 88 of which, after directing inflating liquid into the balloon 80, can inject contrast material into the balloon 80 so that x-rays can be taken of the balloon with the inflating material therewithin to determine the proper placement of the balloon. Alternatively, the inflation liquid could comprise a radiopaque inflation liquid, such as Conray® contrast medium (commercially available from Mallinckrodt Inc. of St. Louis, Mo.), such that inflation and visualization can be done concurrently, allowing monitoring of the balloon position and condition during the inflation step. Tube 16 is also shown in FIG. 6, it being attached in some suitable manner to the outer side wall surface of tube 88.

Figure 3:
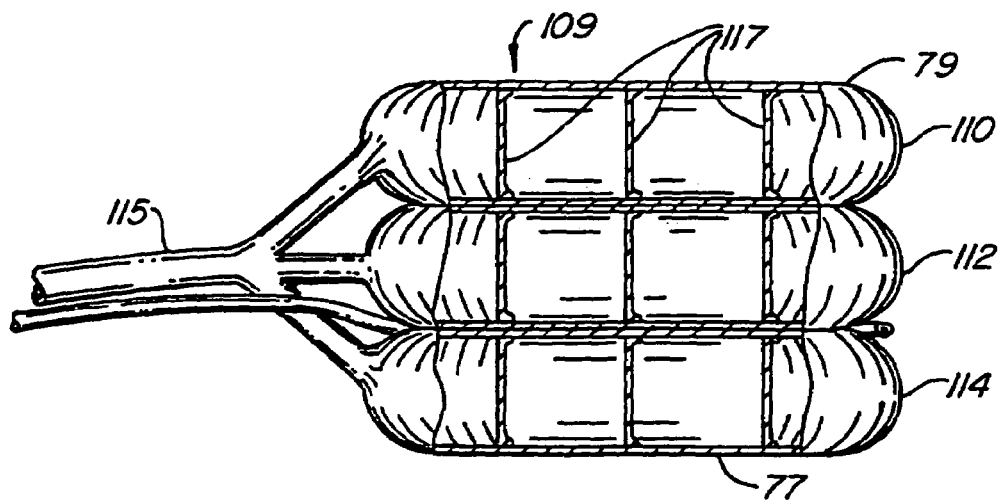
FIG. 3 is a schematic view of another embodiment of the balloon of the present invention showing three stacked balloons and string-like restraints for limiting the expansion of the balloon in various directions of inflation.

Still another embodiment of the invention is shown in FIG. 3, which is similar to FIG. 1 (although at least one difference is that it is not a single doughnut) and includes an inflatable device 109 having three balloon units 110, 112 and 114 which are inflatable and which have string-like restraints 117 which limit the expansion of the balloon units in a direction transverse to the longitudinal axes of the balloon units. If desired, the restraints can comprise the same or a similar material as the balloon, or the restraints can comprise a material having a reduced, little or no substantial expansion capability.

A tube system 115 can be provided to direct liquid under pressure into the balloon units 110, 112 and 114 so that liquid can be used to inflate the balloon units when placed inside the bone in a deflated state. Following the proper inflation and compaction of the bone marrow, the balloon(s) can be removed by deflating it/them and pulling it/them outwardly of the bone being treated. The restraints desirably keep the opposed sides 77 and 79 substantially flat and parallel with respect to each other.

Figure 10:
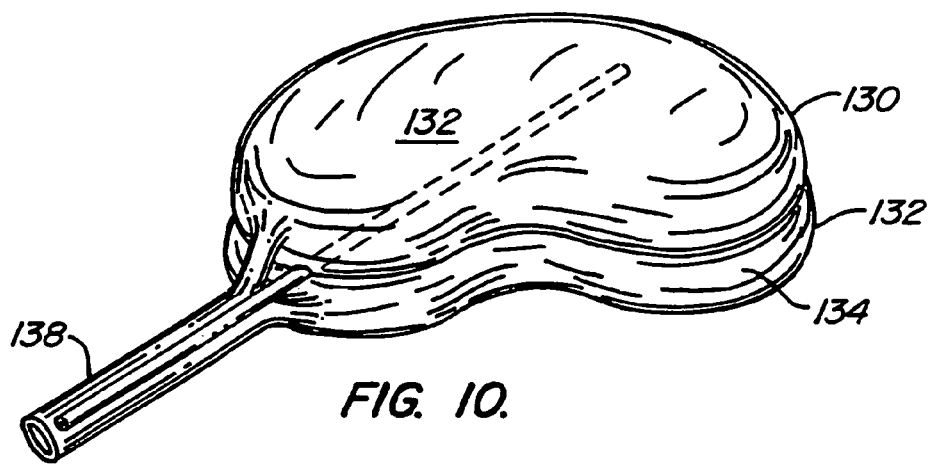
FIG. 10 is a perspective view of another embodiment of a balloon of the present invention formed in the shape of a kidney bean.
Figure 11:
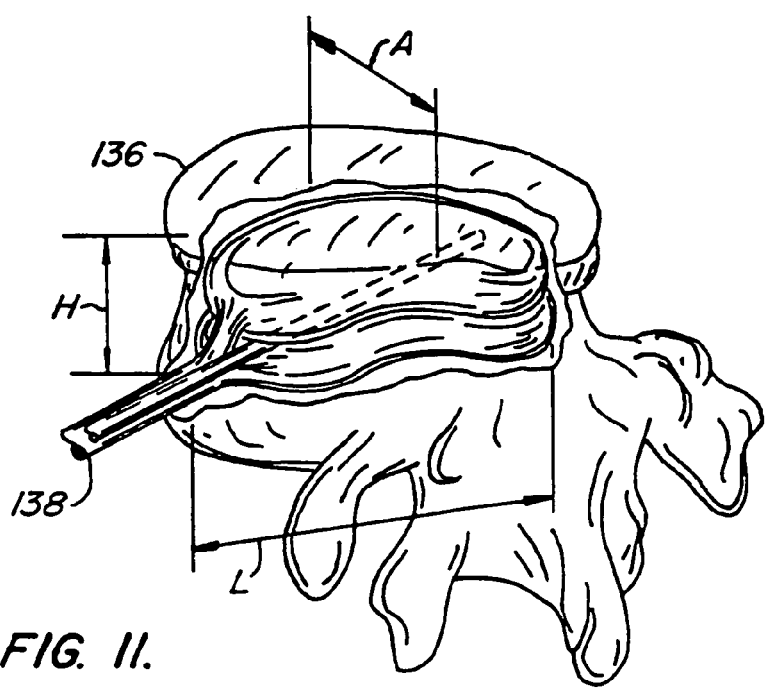
FIG. 11 is a perspective view of the vertebral bone showing the kidney shaped balloon of FIG. 10 inserted in the bone and expanded.

In FIG. 10, another embodiment of the inflatable balloon is shown. The device comprises a kidney shaped balloon body 130 having a pair of opposed kidney shaped side walls 132 which are adapted to be collapsed and to cooperate with a continuous end wall 134 so that the balloon 130 can be forced into a bone 136 shown in FIG. 11. A tube 138 is used to direct inflating liquid into the balloon to inflate the balloon and cause it to assume the dimensions and location shown in the vertebral body 136 in FIG. 11. The balloon 130 will desirably compress the cancellous bone if there is no fracture or collapse of the cortical bone. The restraints for this action are principally due to the side and end walls of the balloon.

Figure 12:
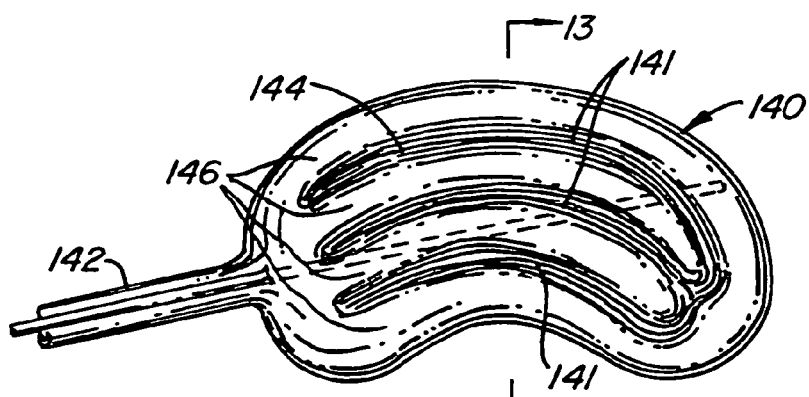
FIG. 12 is a top view of a kidney shaped balloon formed of several compartments by a heating element or branding tool.
Figure 13:
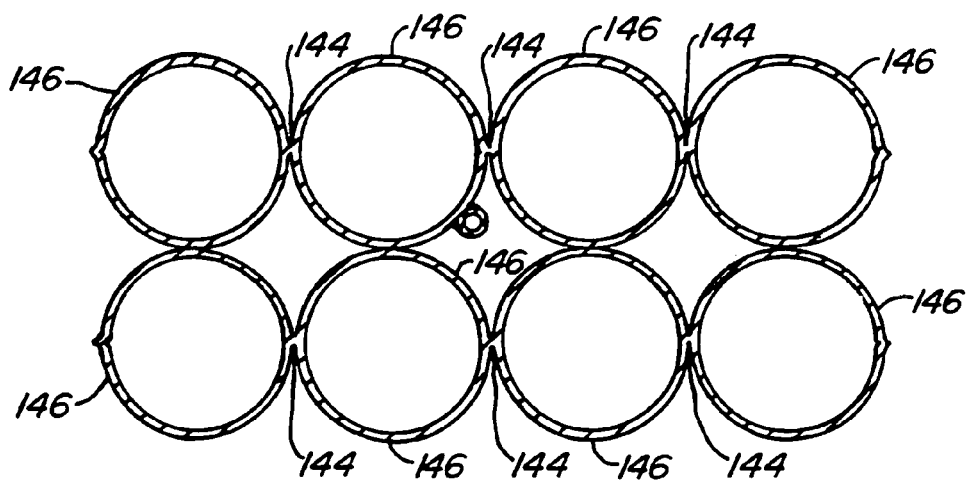
FIG. 13 is a cross-sectional view taken along line 13-13 of FIG. 12, showing two kidney shaped balloons that have been stacked.

FIG. 12 shows a balloon 140 which is also kidney shaped and has a tube 142 for directing an inflatable liquid into the tube for inflating the balloon. The balloon is initially formed in the shape of a single chamber bladder but the bladder can subsequently be compressed, branded or melted along curved lines or strips 141 to form attachment lines 144 which take the shape of side-by-side compartments 146 which are kidney shaped as shown in FIG. 13. The branding desirably causes a welding and/or bonding of the two sides of the bladder—the material can be standard medical balloon material, which is typically plastic that can be formed and/or bonded using heat.

Figure 14:
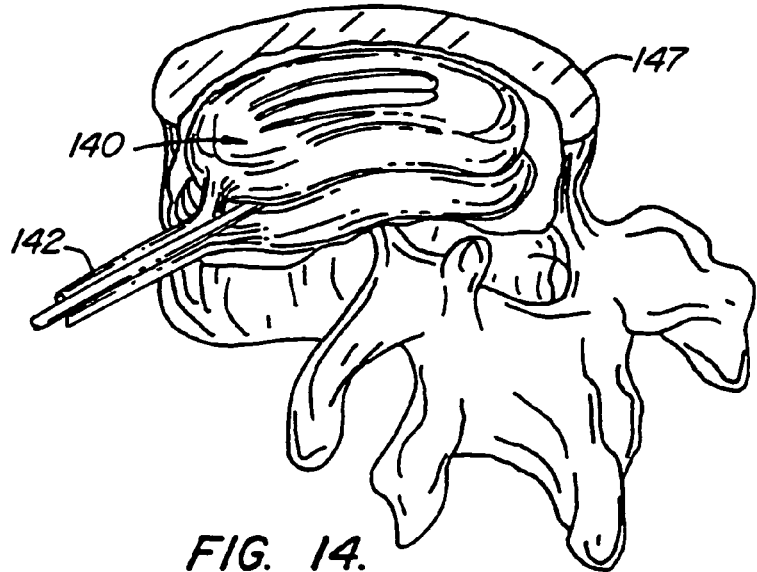
FIG. 14 is a view similar to FIG. 11 but showing the stacked kidney shaped balloon of FIG. 13 in the vertebral bone.

FIG. 14 is a perspective view of a vertebral body 147 containing the balloon of FIG. 12, showing a double stacked balloon 140 when it is inserted in vertebral bone 147.

Figure 15:
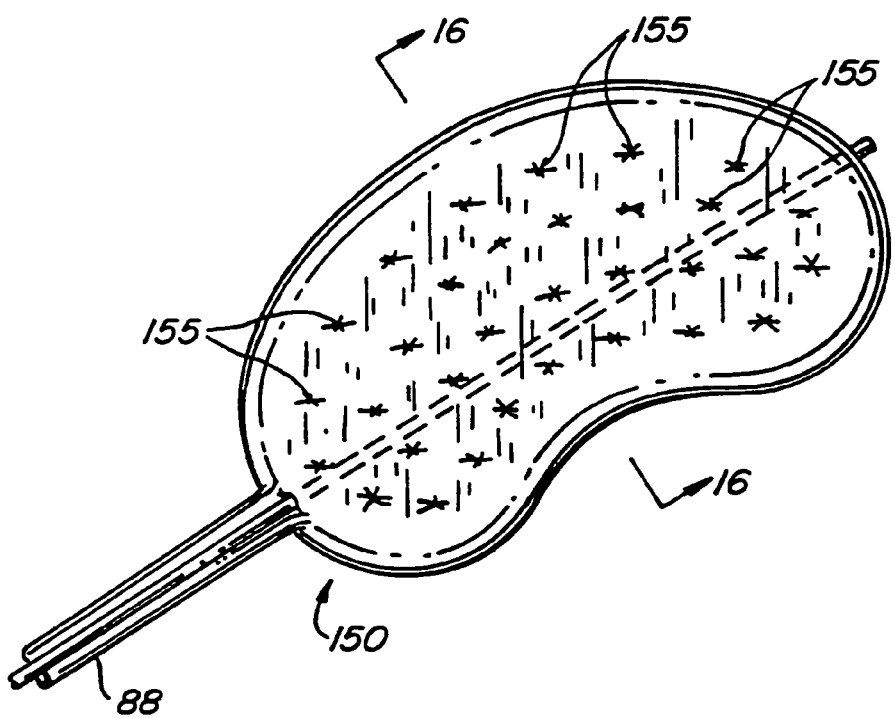
FIG. 15 is a top view of a kidney shaped balloon showing outer tufts holding inner strings in place interconnecting the top and bottom walls of the balloon.
Figure 16:
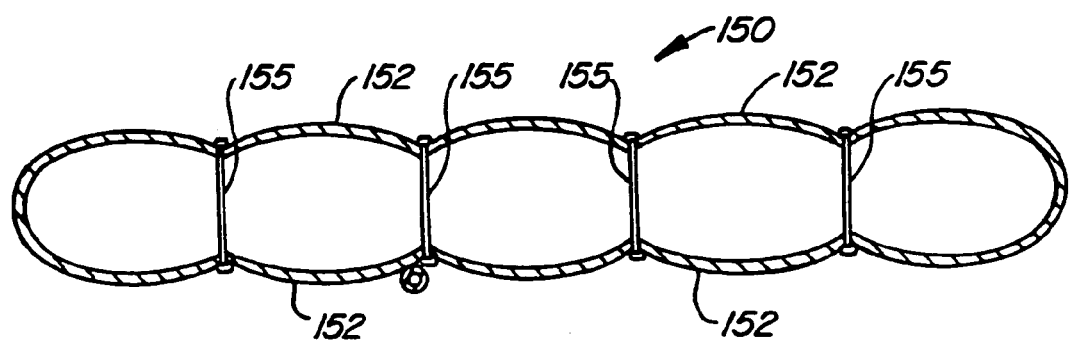
FIG. 16 is a cross-sectional view taken along line 16-16 of FIG. 15.

FIG. 15 is a view of a balloon similar to that of FIG. 10 except that tufts 155, which can be string-like restraints or other structures extending between the opposing inner walls of the balloon, extend between and are connected to the side walls 152 of the inflatable device 150 and desirably limit or constrain (to some degree) the expansion of the side walls with respect to each other. In this embodiment, the tufts desirably render the side walls generally parallel with each other. Of course, tufts which merely limit and/or reduce the displacement between opposing walls of the balloon will similarly accomplish various objectives of the present invention to some degree. Tube 88 is used to fill the kidney shaped balloon with an inflating liquid in the manner described above.

The dimensions for a vertebral body balloon can vary across a broad range, depending upon the size, location, and condition of the targeted vertebral body as well as the objectives of the treatment. For example, the height H (FIG. 11) of a vertebral body balloon for both lumbar and thoracic vertebral bodies can typically range from 0.5 cm to 3.5 cm. The anterior to posterior vertebral body balloon dimension A (FIG. 11) for both lumbar and thoracic vertebral bodies can typically range from 0.5 cm to 3.5 cm. The side to side vertebral body dimension L (FIG. 11) for thoracic vertebral bodies will often range from 0.5 cm to 3.5 cm. The side to side vertebral body dimensions for lumbar vertebral bodies will typically range from 0.5 cm to 5.0 cm. Of course, depending upon the objectives of the treatment and the actual dimensions of the patient's bones, the use of balloons having larger or smaller dimensions than these disclosed ranges may be appropriate.

The eventual selection of the appropriate balloon for, for instance, a given vertebral body is based upon several factors. One major factor affecting the choice of balloon size is the objectives of the treatment. For example, if the principal treatment objective is simply the repair and/or augmentation of a collapsed vertebral body, then the appropriate balloon size (and desired cavity size) may be a balloon which is less than or approximates the size of the interior of the vertebral body in an unfractured and/or uncollapsed condition. Alternatively, two or more balloons could be used concurrently within a single vertebral body, which together create a desired size cavity within the vertebral body. As another alternative, if the objective of treatment is more localized within the bone, such as the creation of a smaller cavity to augment and/or repair a smaller section of the bone, then the use of a smaller balloon size (and desired cavity size) may be desirous. Similarly, where the cancellous bone is relatively strong and/or resistant to compression, the use of a smaller balloon may be warranted to accomplish the objective of displacing cortical bone (to reduce the fracture) without significantly compressing the cancellous bone (thus creating a smaller cavity). Moreover, smaller balloons may also be suited for use in the treatment of bone tumors, etc., where the balloon can be used to create a small cavity adjacent to the tumor—this small cavity will simplify the use of other minimally invasive tools to directly visualize the treatment area as well as morselize and/or excise the tumor from the bone.

The anterior-posterior (A-P) balloon dimension is measured from the internal cortical wall of the anterior cortex to the internal cortical wall of the posterior cortex of the vertebral body. In general, for augmentation and/or reinforcement of a collapsed vertebral body, the appropriate A-P balloon dimension will often be approximately 5 to 7 millimeters less than this measurement. In one embodiment, the A-P balloon dimension will be approximately 15 millimeters. In an alternate embodiment, the A-P balloon dimension will be approximately 20 millimeters.

The appropriate side to side balloon dimensions for a given vertebral body is selected from the CT scan or from a plain film x-ray view of the vertebral body to be treated. The side to side distance can be measured from the internal cortical walls of the side of the vertebral bone. In one embodiment, the appropriate side to side balloon dimension may be 5 to 7 millimeters less than this measurement. In alternate embodiments, the appropriate side to side balloon dimensions may be significantly smaller, such as where multiple balloons are introduced into a single vertebral body or where the displacement of cortical bone is a primary objective of the treatment. In general, lumbar vertebral bodies tend to be much wider in their side to side dimension than in their A-P dimension. In contrast, thoracic vertebral bodies are typically approximately equal in their the side to side dimensions and their A-P dimensions.

The height dimensions of the appropriate vertebral body balloon for a given vertebral body may be chosen by the CT scan or x-ray views of the vertebral bodies above and below the vertebral body to be treated. The height of the vertebral bodies above and below the vertebral body to be treated can be measured and averaged. This average may be used to determine the appropriate height dimension of the chosen vertebral body balloon. Of course, as previously mentioned, various other balloon sizes may be desirous based upon the objectives of the treatment, as well as the actual patient's anatomy.

B. Balloons for Long Bones

Long bones which can be treated with the use of balloons of the present invention include (but are not limited to) the distal radius (larger arm bone at the wrist), the proximal tibial plateau (leg bone just below the knee), the proximal humerus (upper end of the arm at the shoulder), and the proximal femoral head (leg bone in the hip). In one embodiment suitable for use in the distal radius or wrist, the longitudinal length of the balloon (such as the embodiment shown in FIG. 27) will be approximately 10 millimeters.

C. Distal Radius Balloon

Figure 17A:
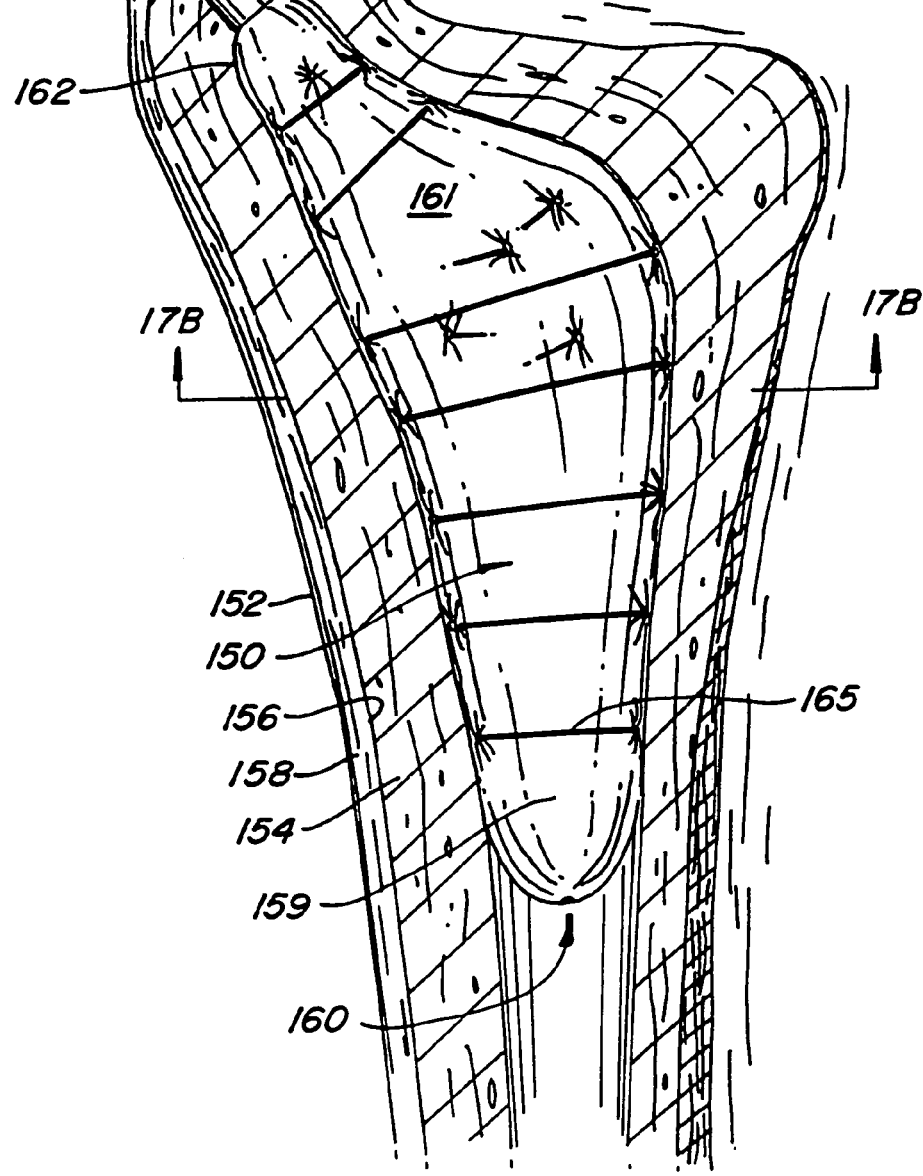
FIG. 17A is a dorsal view of a humpback banana balloon in a right distal radius.

For treatment of the distal radius 152, one embodiment of a balloon 160 shown in FIG. 17*a* has a shape which approximates a pyramid but more closely can be considered the shape of a humpbacked banana in that it substantially fills the interior of the space of the distal radius to force cancellous bone 154 against the inner surface 156 or cortical bone 158.

Figure 17B:
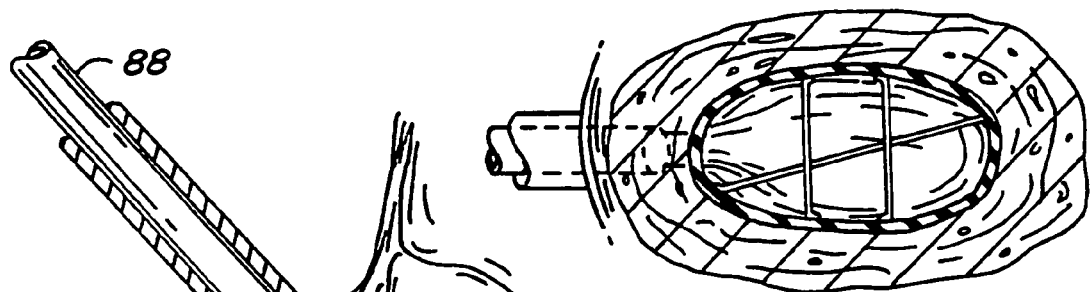
FIG. 17B is a cross-sectional view of FIG. 17A taken along line 17B-17B of FIG. 17A.

The balloon 160 has a lower, conical portion 159 which extends downwardly into the hollow space of the distal radius 152, and this conical portion 159 increases in cross section as a central distal portion 161 is approached. The cross section of the balloon 160 is shown at a central location (FIG. 17B) and this location is near the widest location of the balloon. The upper end of the balloon, denoted by the numeral 162, converges to the catheter 88 for directing a liquid into the balloon for inflating the same to compress the cancellous bone and/or force the cancellous bone against the inner surface of the cortical bone. The shape of the balloon 160 can desirably be predetermined and can be restrained by tufts formed by string restraints 165, as well as various other types of restraints described herein. These restraints are optional and provide additional strength to the balloon body 160, but are not absolutely required to achieve the desired configuration. The balloon is placed into and taken out of the distal radius in the same manner as that described above with respect to the vertebral bone.

The dimensions of the distal radius balloon vary as follows:

The proximal end of the balloon (i.e. the part nearest the elbow) is cylindrical in shape and will vary from 0.5'0.5 cm to 1.8'1.8 cm.

The length of the distal radius balloon will vary from 1.0 cm to 12.0 cm.

The widest medial to lateral dimension of the distal radius balloon, which occurs at or near the distal radio-ulnar joint, will measure from 1.0 cm to 2.5 cm.

The distal anterior-posterior dimension of the distal radius balloon will vary from 0.5 cm to 3.0 cm.

Figure 25A:
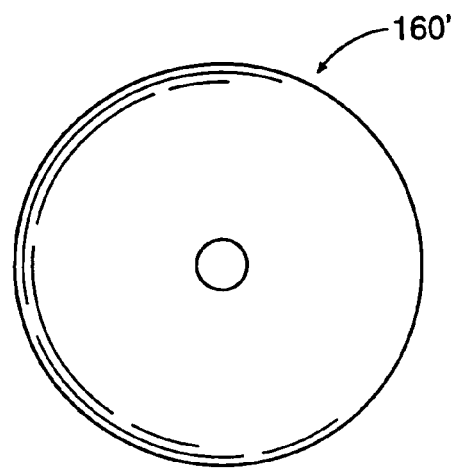
FIG. 25A is a front view of another embodiment of an expandable structure for use in compressing cancellous bone and/or displacing cortical bone.
Figure 25B:
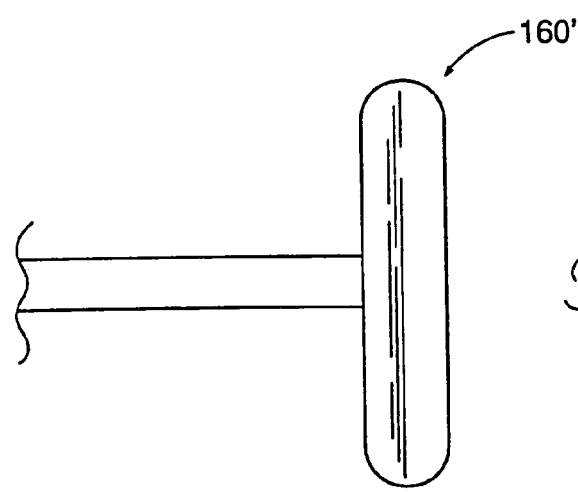
FIG. 25B is a side view of the structure of FIG. 25A.
Figure 25C:
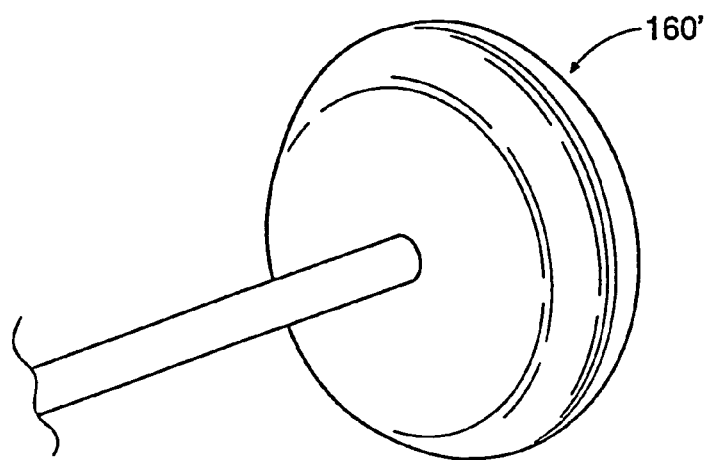
FIG. 25C is a perspective view of the structure of FIG. 25A.
Figure 27:
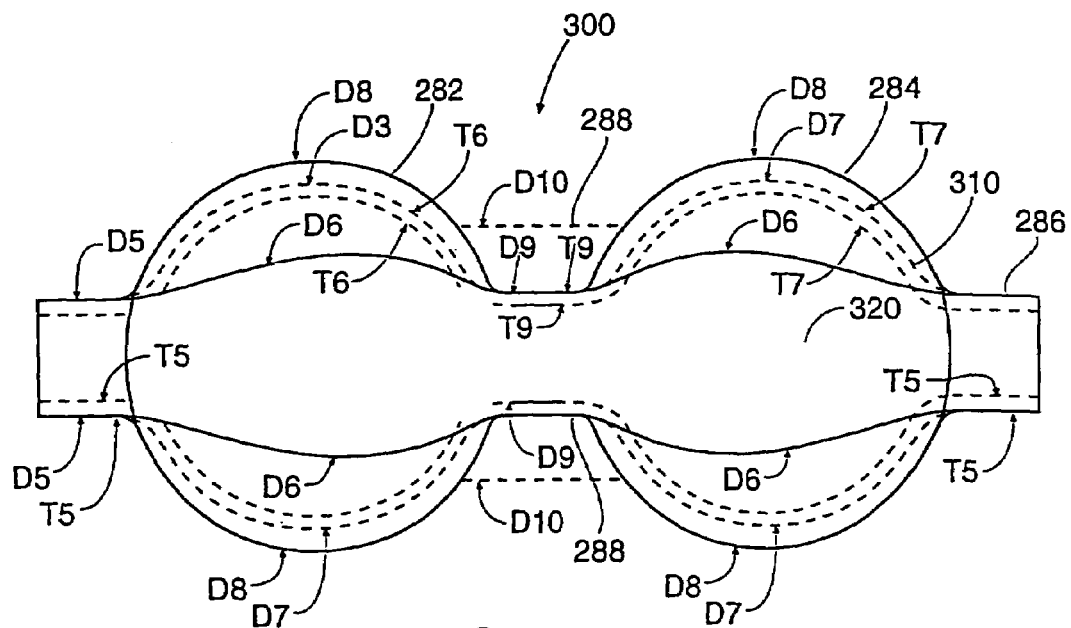
FIG. 27 is another embodiment of an expandable structure.

In an alternate embodiment also suited for use in treating a distal radius fracture, a balloon can take the shape of a toroidal or disk-like shape, such as shown in FIGS. 25A☐25C. As previously noted, another alternate embodiment of a balloon suited for use in treating a distal radius is shown in FIG. 27. Of course, the selection of the appropriate balloon size to treat a given fracture of the distal radius will often depend on the radiological size of the distal radius and the location of the fracture, as well as the treatment goals.

D. Proximal Humerus Fracture Balloon

Figure 18:
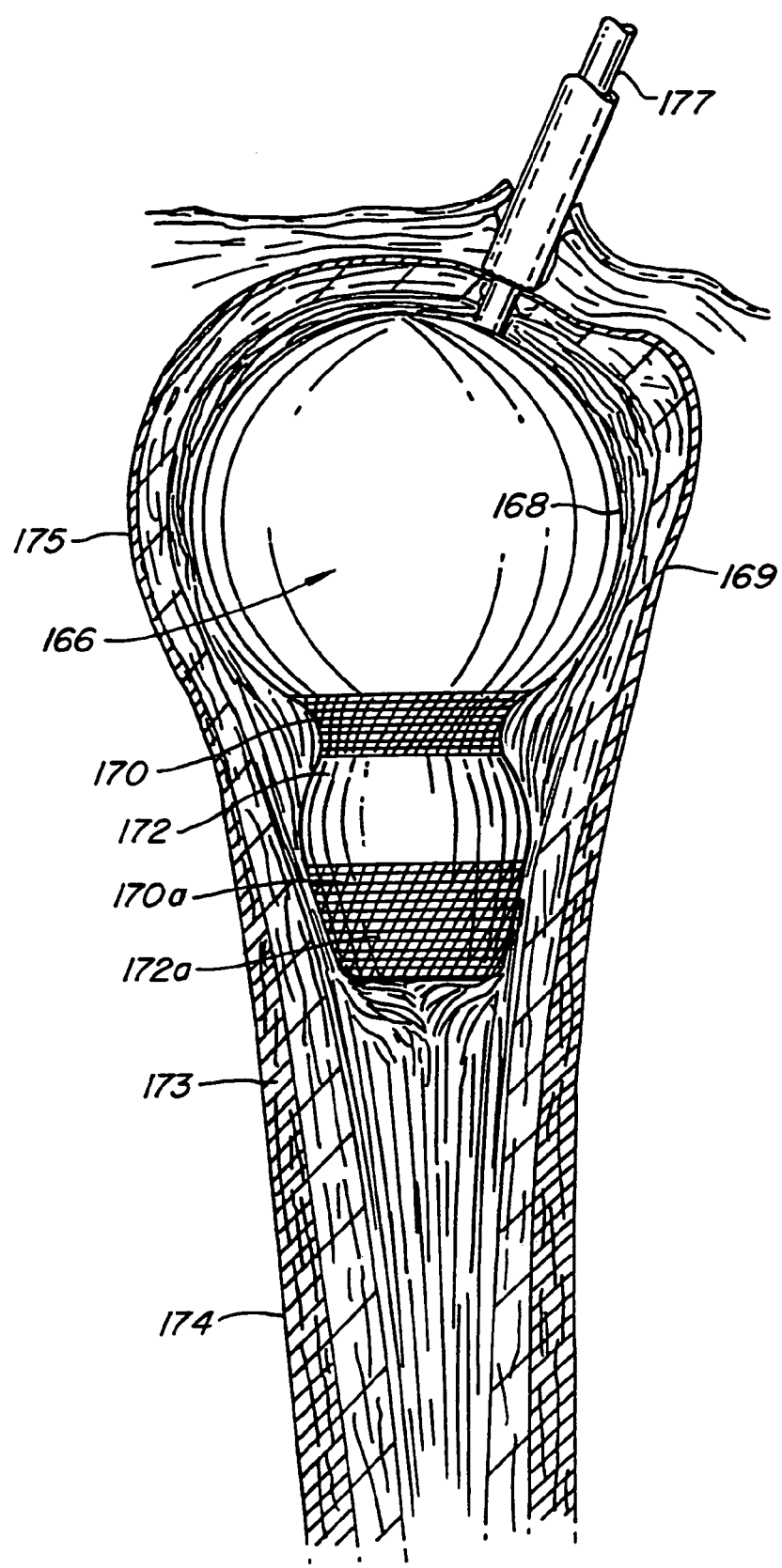
FIG. 18 is a spherical balloon with a base in a proximal humerus viewed from the front (anterior) of the left proximal humerus.

In the case of the proximal humerus 169, one embodiment of a balloon 166 shown in FIG. 18 is spherical and has a base design. It can optimally compact the cancellous bone 168 in a proximal humerus 169. A mesh 170, embedded, laminated and/or wound, may be used to form a neck 172 on the balloon 166, and a second mesh 170*a* may be used to conform the bottom of the base 172*a* to the shape of the inner cortical wall at the start of the shaft. These restraints provide additional strength to the balloon body, but the configuration can be achieved through various methods, including molding of the balloon body or various other restraints described herein. This embodiment desirably compresses the cancellous bone to create a compacted region surrounding the balloon 166 as shown in FIG. 18. The cortical bone 173 is desirably relatively wide at the base 174 and is thin-walled at the upper end 175. The balloon 166 has a feed tube 177 into which liquid under pressure is forced into the balloon to inflate it to compact the cancellous bone in the proximal humerus. The balloon is inserted into and taken out of the proximal humerus in the same manner as that described above with respect to the vertebral bone.

In this embodiment, the dimensions of the proximal humerus fracture balloon vary as follows:

The spherical end of the balloon will vary from 1.0'1.0 cm to 3.0'3.0 cm.

The neck of the proximal humeral fracture balloon will vary from 0.8'0.8 cm to 3.0'3.0 cm.

The width of the base portion or distal portion of the proximal humeral fracture balloon will vary from 0.5'0.5 cm to 2.5'2.5 cm.

The length of the balloon will vary from 4.0 cm to 14.0 cm.

Figure 18A:
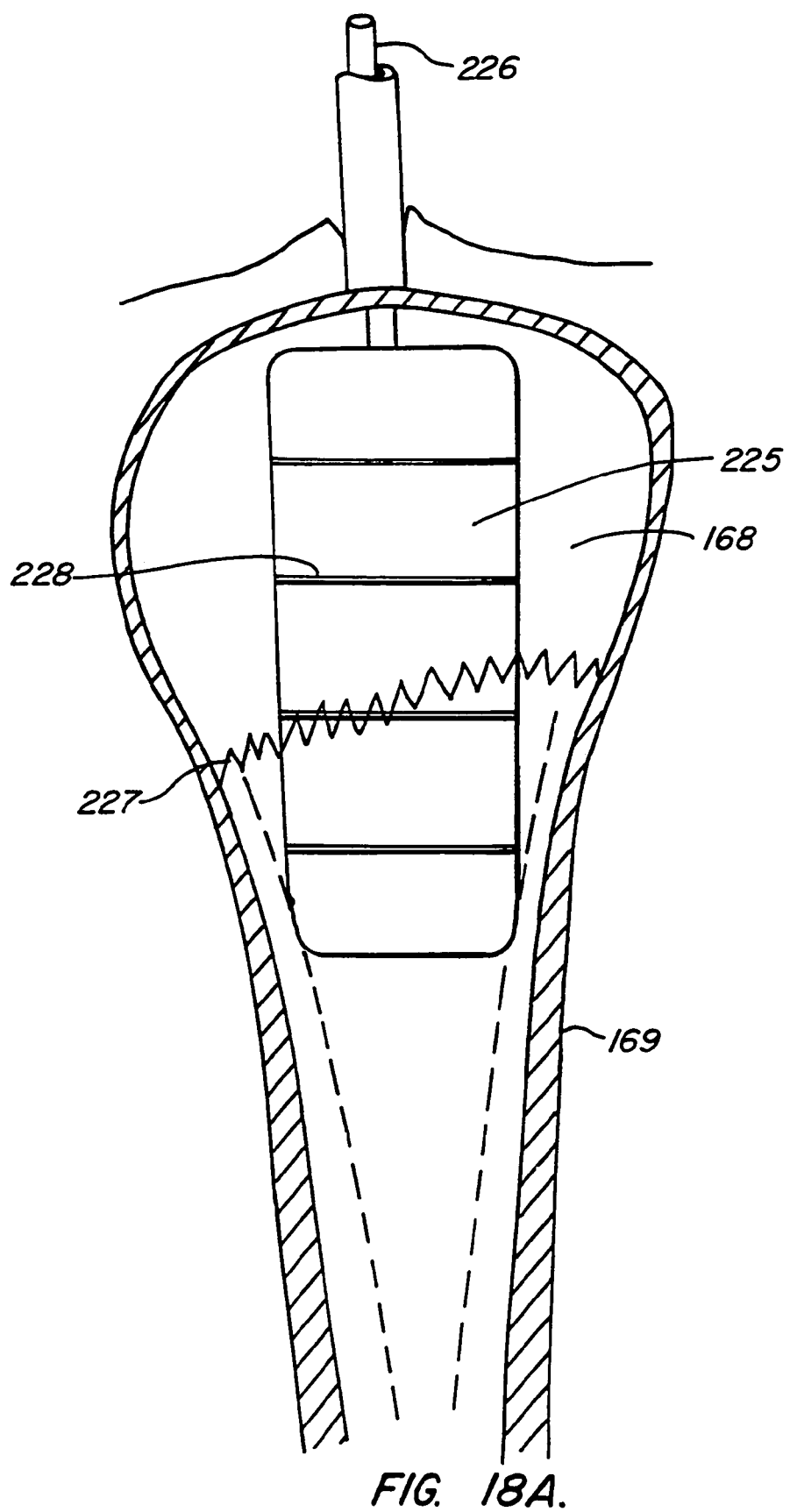
FIG. 18A is an alternate embodiment of a balloon for use in a long bone such as the proximal humerus, constructed in accordance with the teachings of the present invention.

An alternate embodiment of a balloon for treating a fracture of various long bones, including a proximal humerus, is shown in FIG. 18A. In this embodiment, the balloon 225 is desirably formed in the shape of a cylinder, with a series of windings or bands 228 extending around the periphery of the balloon 225 to constrain the expansion of the balloon 225. Desirably, the balloon will extend within the long bone across both sides of the fracture 227, thereby stabilizing the surrounding cortical bone 169 and permitting the bone to quickly reassume at least limited loading.

Of course, the selection of the appropriate balloon to treat a given proximal humeral fracture depends on the radiologic size of the proximal humerus and the location of the fracture as well as the treatment goals.

E. Proximal Tibial Plateau Fracture Balloon

Figure 19A:
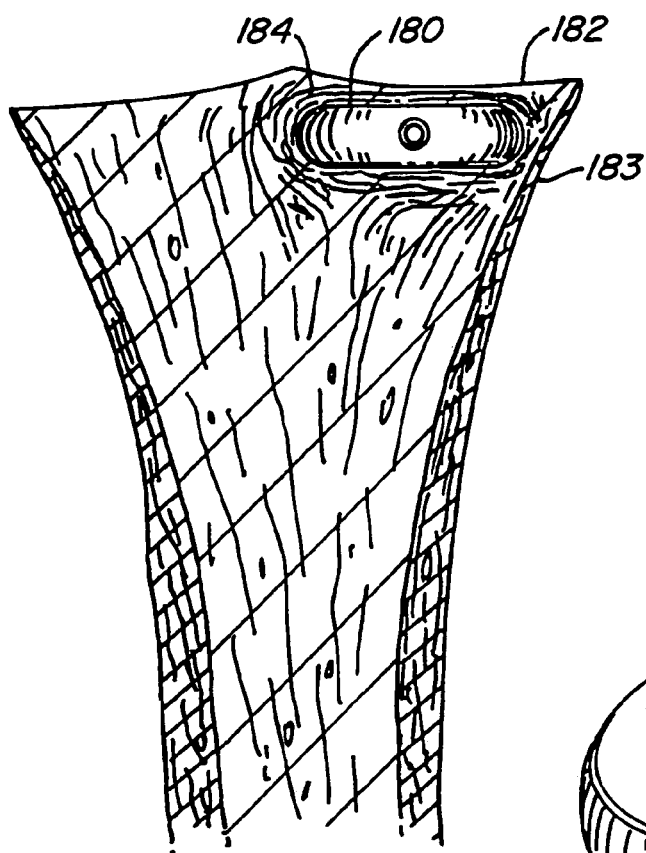
FIG. 19A is the front (anterior) view of the proximal tibia with the elliptical cylinder balloon introduced beneath the medial tibial plateau.
Figure 19B:
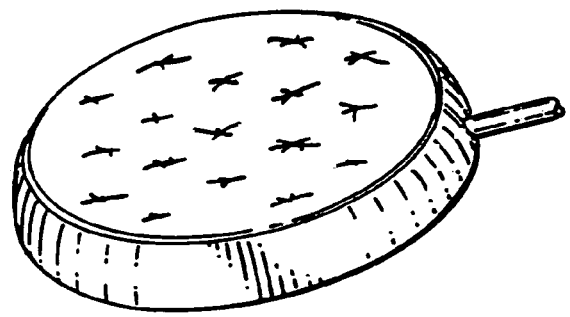
FIG. 19B is a three-quarter view of the balloon of FIG. 19A.
Figure 19C:
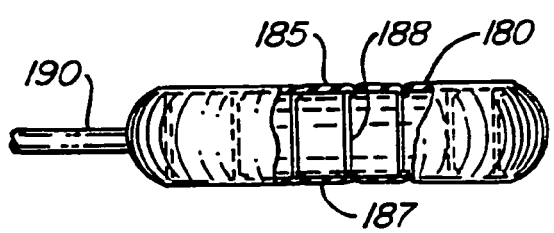
FIG. 19C is a side elevational view of the balloon of FIG. 19A.
Figure 19D:
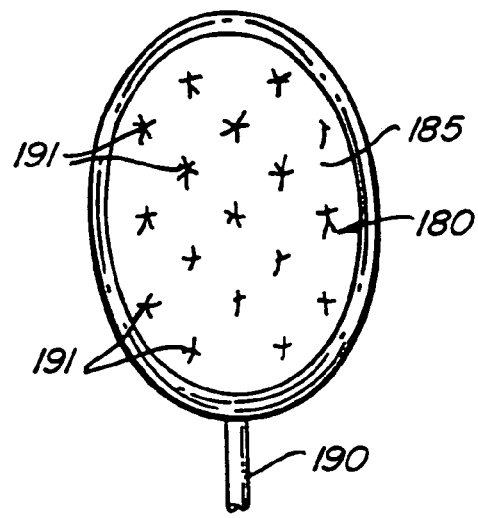
FIG. 19D is a top plan view of an alternate embodiment of the balloon of FIG. 19A.

FIG. 19A shows one embodiment of a balloon 180 suitable for treating a tibial fracture, where the balloon 180 is placed in one side 182 of a tibia 183. Desirably, the balloon, when inflated, compacts the cancellous bone in the layer 184 surrounding the balloon 180 and/or lifts or displaces the fractured cortical bone fragments towards their proper anatomical positions. A cross section of this embodiment of a balloon is shown in FIG. 19C wherein the balloon has a pair of opposed sides 185 and 187 which are interconnected by restraints 188 which can be in the form of strings or flexible members of any suitable construction. In this embodiment, the restraints desirably maintain the sides 185 and 187 substantially parallel with each other and non-spherical. A tube 190 is coupled to the balloon 180 to direct inflation liquid into and out of the balloon. The ends of the restraints are shown in FIGS. 19B and 19D and denoted by the numeral 191. The balloon is inserted into and taken out of the tibia in the same manner as that described above with respect to the vertebral bone. FIG. 19B shows a substantially circular configuration for the balloon; whereas, FIG. 19D shows a substantially elliptical version of the balloon.

The dimensions of this embodiment of a proximal tibial plateau fracture balloon vary as follows:

The thickness or height of the balloon will vary from 0.5 cm to 5.0 cm.

The anterior-posterior (front to back) dimension will vary from 1.0 cm to 6.0 cm.

The side to side (medial to lateral) dimension will vary from 1.0 cm to 6.0 cm.

The selection of the appropriate balloon to treat a given tibial plateau fracture will depend on the radiological size of the proximal tibial and the location of the fracture, as well as the treatment goals.

F. Femoral Head Balloon

Figures 20, 20A:
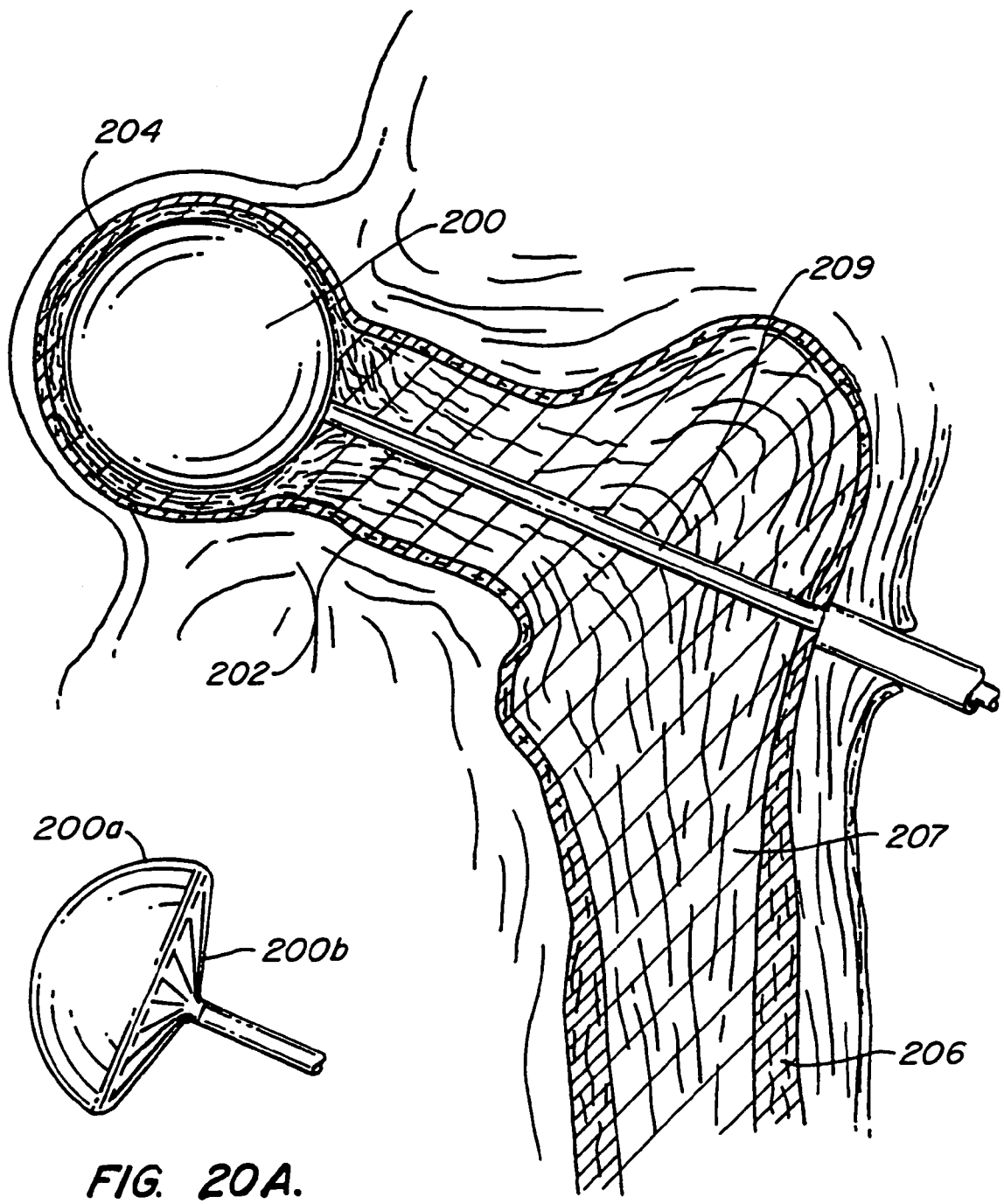
FIG. 20 is a spherically shaped balloon for treating avascular necrosis of the head of the femur (or humerus) as seen from the front (anterior) of the left hip.
FIG. 20A is a side view of a hemispherically shaped balloon for treating avascular necrosis of the head of the femur (or humerus).

In the case of a fracture or collapse of a femoral head, one embodiment of a balloon 200, shown in FIG. 20, is inserted inside the cortical bone 202 of the femoral head which is thin at the outer end 204 of the femur and which can increase in thickness at the lower end 206 of the femur. The cortical bone surrounds the cancellous bone 207, with the cancellous bone desirably compacted by the inflation of the balloon 200. The tube for directing liquid for inflation purposes into the balloon is denoted by the numeral 209. It extends along the femoral neck and is directed into the femoral head which is generally spherical in configuration. FIG. 20A shows that the balloon, denoted by the numeral 200a, can be hemispherical as well as spherical, as shown in FIG. 20. The balloon 200 is inserted into and taken out of the femoral head in the same manner as that described with respect to the vertebral bone. The hemispherical shape is maintained in this example by bonding overlapping portions of the bottom, creating pleats 200b as shown in FIG. 20A.

The diameter of the femoral head balloon may vary from 1.0 cm to up to 4.5 cm or greater. The appropriate size of the femoral head balloon to be chosen depends on the radiological or CT scan size of the head of the femur and/or the location and size of the avascular necrotic bone. The dimensions of the hemispherical balloon are similar to those of the spherical balloon, except that approximately one half of the balloon is provided.

G. Prevention of Hip Fracture

Figure 21:
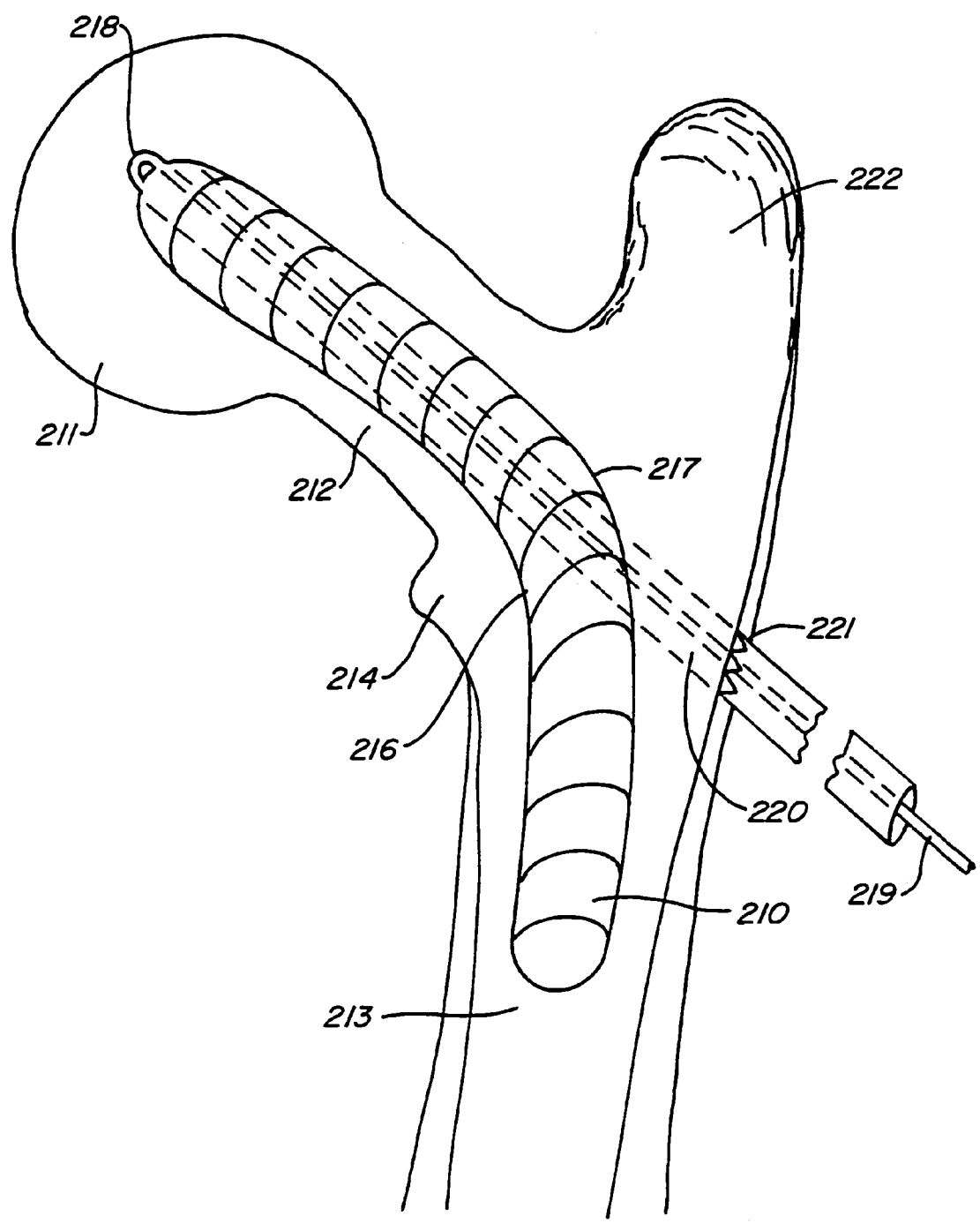
FIG. 21 is a balloon for preventing and/or treating hip fracture as seen from the anterior (front) of the left hip.
Figure 23:
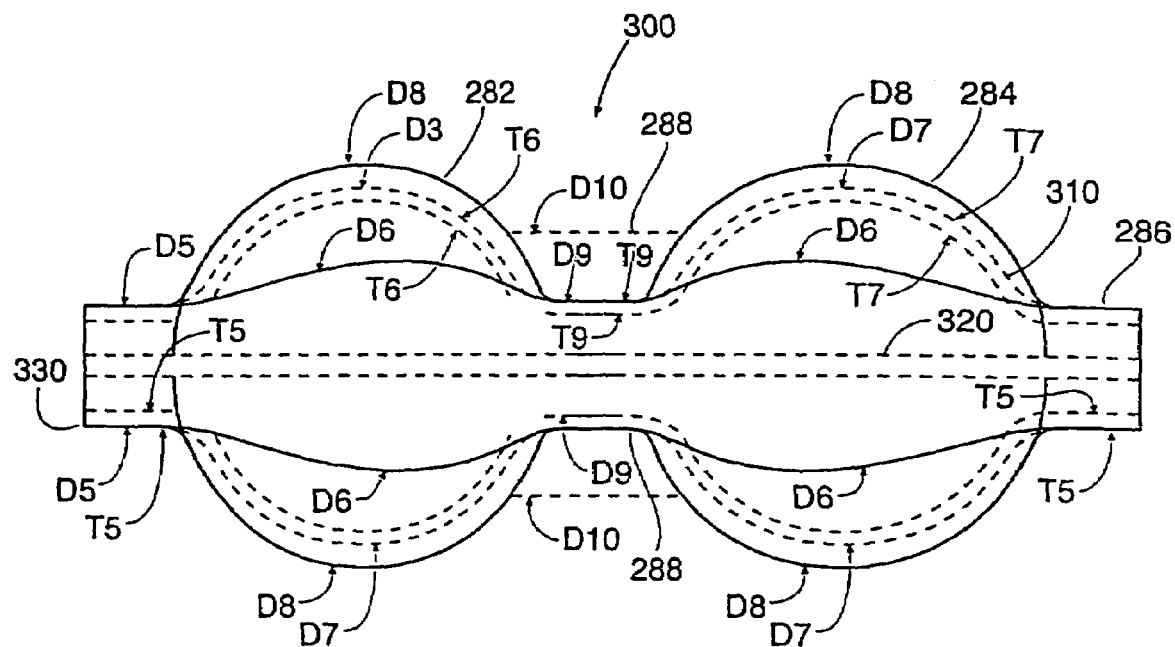
FIG. 23 is another embodiment of an expandable structure incorporating an internal expansion restraint.

FIG. 21 illustrates one embodiment of a "boomerang" balloon 210 adapted for preventing and/or treating hip fracture. When inflated, the "boomerang" balloon 210 is desirably a cylinder which gradually bends in the middle, like a boomerang, and extends from about 0.5 cm from the end of the femoral head 211 through the femoral neck 212 and down into the proximal femoral diaphysis 213 about 5-7 cm past the lesser trochanter 214. This embodiment of a balloon 210 preferably maintains its shape by rings 215 of inelastic or semi-elastic material held closer together on one side by attachment to a shorter inelastic or semi-elastic band 216 running the length of the side of balloon and further apart by attachment to a longer inelastic or semi-elastic band 217 bonded on the opposite side, although various other restraints disclosed herein would also suffice.

After and prior to inflation, the balloon 210 may be folded back (shown in dotted lines at 218) against the inflation tube 219. Prior to inflation, the balloon 210 can also be rolled up and held against the inflation tube with loose attachments that break when the balloon is inflated. To insert the balloon on its inflation tube into the hip, the surgeon can use a power drill under radiographic guidance to create a cavity 220 that is usually 4-6 mm wide starting at the lateral femoral cortex 221 and proceeding into the femoral head 211. Inflation of the balloon 210 into the greater trochanteric region 222 instead of down the femoral diaphysis 213 is less desirable and is typically avoided by proper choices in the shape of the balloon as well as by its placement and correct orientation (the deflated balloon desirably facing the lesser trochanter). After the balloon 210 has been inflated within the cavity 220 (see the dotted lines in FIG. 21), the predetermined size and shape of the balloon biases the proximal portion of the balloon downward into the lesser trochanter. Optionally, a second cavity can be drilled down into the diaphysis, starting from the same entry point or from the other side.

Patients with bone density in the hip below a threshold value are at increased risk of hip fracture, and lower densities create greater risk. Patient selection may be done through a bone density scan or other methods of determining bone quality well known in the art. Such selection could also result from a previous and/or concurrent fracture of the other hip, or some other type and/or location of osteoporotic fracture. The balloon length can be chosen by the surgeon to extend about 0.5 cm from the end of the femoral head, through the femoral neck and into the proximal femoral diaphysis, usually about 4-8 cm below the lesser trochanter. The balloon diameter can be chosen by measuring the inner cortical diameter of the femoral neck (the most narrow area) and subtracting 0.5 cm. The preferred dimensions of the "boomerang" balloon are a total length of 10-20 cm and a diameter of 1.0-2.5 cm. (A "humpback banana" balloon with appropriate length may also be useful in hip fracture prevention, where the "humpback" width does not exceed the desired femoral neck dimensions.)

Patients having the lowest bone densities in the femoral head may require greater compacting in the femoral head, which may, for example, be provided by using two balloons, one after the other: the "boomerang" followed by the femoral head balloon (inserted at the same point and expanded prior to inserting any supporting material.) Alternatively, the "boomerang" balloon may be adapted to have a distal portion that approximates the shape of the femoral head balloon.

The various balloons described herein could also be used in conjunction with the replacement of various structures within human and animal bodies. For example, the balloons described herein could be used to compress cancellous bone in a femur in preparation for the implantation of an artificial hip stem. Similarly, the balloons described herein could be used in conjunction with various other joint replacement procedures, including artificial knee and ankle joints. In addition, metal reinforcing members, such as stents or reinforcing bar (rebar) could be used to reinforce the filler material contained within the cavity.

H. All Balloons

It should be understood that the various embodiments of balloons disclosed herein are by no means limited in their utility to use in a single treatment location within the body. Rather, while each embodiment may be disclosed in connection with an exemplary treatment location, these embodiments can be utilized in various locations within the human body, depending upon the treatment goals as well as the anatomy of the targeted bone. For example, the embodiment of a balloon previously disclosed as useful in treating a fracture of the distal radius could similarly be used in the treatment of fractures in various other areas within the body, including but not limited to fractures and/or impending fractures of the femur, the radius, the ulna, the tibia, the humerus, the calcaneus or the spine. Similarly, the various other disclosed embodiments can be utilized throughout the body, with varying results depending upon treatment goals and/or the anatomy of the targeted bone.

II. The Inflatable Device

A. Complex Expandable Structures

Sometimes it can be difficult to achieve a desired uniformity and area of compaction within a given cancellous bone region using an expandable body having a single expansion region. FIG. 27 shows one embodiment of a complex preformed structure 300 which includes expandable regions 282, 284 and 288 spaced along its length. The structure 280 desirably increases in volume along substantially its entire profile in a non-spherical manner.

The complex expandable structure is created by extruding or molding a tube 286 of polyurethane plastic or other elastomer material. In a preferred embodiment, the tube is comprised of polyurethane plastic material. The tube has a normal extruded wall thickness (T5) and a normal extruded outside diameter (D5).

The shaped regions 282, 284 and 288 are created by exposing an intermediate region of the tube to heat, positive interior pressure and/or stretching inside a fixture or mold (not shown). In one embodiment, the fixture could possess two expanded cavity regions separated by a reduced diameter region or intermediate channel. The cavity regions and the channel can be exposed to a source of heat, to soften the material of the region. When heat-softened (in the manner previously described), the interior of the tube 286 is stretched and subjected to positive pressure from a source. The material in the neck region 288 will also desirably expand or extend within the cavities and the channel.

Figure 28:
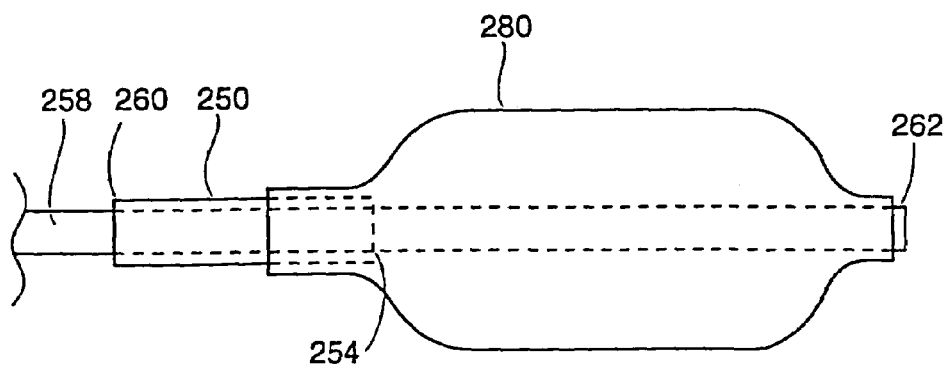
FIG. 28 is a side view of the distal tip of a cavity-forming device.

Once cooled and removed from the fixture, the structure 280 can be attached to the distal end of an outer catheter tube 250. (See FIG. 28.) The structure of the outer catheter tube 250 (as well as the inner catheter tube 258) can vary, and the catheter tubes 250 and 258 can comprise various flexible materials, including medical grade plastic materials like vinyl, polyethylenes, ionomer, polyurethane, and polytetrapthalate (PET) as well as less flexible materials such as Kevlar®, PEBAX™, stainless steel, nickel-titanium alloys, and other metals and/or ceramics. The outer catheter tube 250 desirably incorporates an interior bore 260, into which an inner catheter tube 258 extends. It should be appreciated that the outer catheter tube 250 can have one or more interior lumens. In the illustrated embodiment, the inner catheter tube 258 extends through the interior bore 260 and beyond the distal end 254 of the catheter tube 250. A proximal end region of the structure 280 is secured to the to the distal end region 254 of the outer catheter tube 250, while a distal end region of the structure 280 is secured to the distal end region 262 of the inner catheter tube 258. The end regions can be secured, e.g., using adhesive or thermal bonding, etc.

The structure 280 possesses, in an open air environment, a normal expanded shape, having diameter D7 (shown in phantom lines of FIG. 27). The normal shape and diameter D7 for the regions 282 and 284 generally correspond with the shape and dimension of the cavities of the mold in which they were formed, respectively.

When an interior vacuum is drawn, removing air and/or fluid from the structure 280, the structure 280 assumes a substantially collapsed, and not inflated, geometry, shown as lines D6 in FIG. 27. Due to the application of heat and pressure upon the intermediate or neck region 288, the diameter D6 for each region 282 and 284 is larger than the normally extruded or molded outside diameter D5 of the original extruded tube.

The regions 282 and 284 are separated by the neck region 288, which segments the structure 280 into two expandable regions 282 and 284. When substantially collapsed under vacuum or not inflated, the structure 280 exhibits a low profile, ideal for the insertion into and/or removal from the targeted cancellous bone region.

The introduction of fluid volume back into the tube 286 will cause each region 282 and 284 to return from the collapsed diameter D6 to the normal, enlarged, but not distended, geometry, having the shape and diameter shown in phantom lines D7 in FIG. 27.

In the illustrated embodiment, the first and second shaped regions 282 and 284 have generally the same radius of expansion and thus the same non-distended shape and diameter D7. Alternatively, each region 282 and 284 can have a different radius of expansion, and thus a different non-distended shape and diameter. Regardless, when in the normal, non-distended diameter D7, the material of the structure 280 in the neck region 288 is not significantly stretched or stressed, because the regions 282 and 284 have been expanded in a stress-relieved condition into these geometries in the cavities.

As before explained in conjunction with the structure, the regions 282 and 284 can be shaped by heat and/or interior pressure within different cavities to assume different geometry's, e.g., cylindrical or elliptical geometry, or a non-spherical, non-cylindrical, or non-elliptical geometry, with either uniform or complex curvature, and in either symmetric or asymmetric forms. Of course, more than two segmented regions 282 and 284 can be formed along the length of the tube. In addition, the normally expanded shape characteristics of the structure can be achieved by other techniques. For example, and not by way of limitation, the structure can be formed by dipping, lost wax casting, or injection molding.

Each shaped region 282 and 284 possesses a minimum wall thickness (designated T7 in FIG. 27) when in the normally enlarged but not distended geometry D7. Due to expansion of heat-softened material under pressure in the cavities, the wall thickness is not uniform, i.e., T7 is less than the normal extruded or molded wall thickness T5 of the tube. The minimum wall thickness T7 for the regions 282 and 284 can be the same or different.

When in the enlarged, but not distended geometry, the neck region 288 has an outside diameter (designated D9 in FIG. 27), which is equal to or greater than the normal extruded or molded diameter D5 of the tube. The size of the channel in the fixture determines the magnitude of the diameter D9. Due to expansion of heat-softened material in the adjacent regions 282 and 284 (as well as the neck region 288) under pressure in the cavities, the neck region 288 (which expands under pressure in the channel) has a wall thickness (designated T9 in FIG. 27) which is less than or equal to the normal extruded or molded wall thickness T5 of the tube 286, but still typically greater than the minimum wall thickness T7 of either fully shaped region 282 or 284.

The formed complex structure 280 thus possesses regions of non-uniform minimum wall thickness along its length; that is, $T5 \geq T9 \geq T7$. The formed complex structure 280 also provides multiple expandable regions 282 and 284 of the same or different enlarged outside diameters (D7), segmented by a neck region 288, in which D6>D5; D7>D6; and D7>D9.

By continuing to apply fluid volume at a constant pressure at a threshold amount P(t), and thereby increasing the volume within the structure 280, the shaped regions 282 and 284 of the structure 280 will continue to enlarge beyond diameter D7 to a distended shape and geometry, designated D8 in FIG. 27. At this time, the wall thickness T7 typically further decreases. As the regions 282 and 284 approach diameter D8, the diameter D9 of the neck region 288 will likewise increase toward diameter D10, as FIG. 27 shows, providing more uniform, elongated surface contact with cancellous bone.

Enlargement of the structure 280 beyond diameter D7 stretches the material in the regions 282, 284 and 288 beyond their stress-relieved condition, although the distended geometry of the regions 282 and 284 will, in important respects, maintain the preformed shape dictated by the cavities.

The degree of stretching at a substantially constant incremental pressure condition can be tailored to achieve a desired, fully distended diameter D8. The final, fully distended diameter D8 can be selected to match the dimensions of the targeted cancellous bone region. The controlled stretching of the segmented regions 282 and 284 in tandem can provide an equal volume compression of cancellous bone with a major diameter that is less than a single non-segmented region (i.e., one without the neck region 288). Stated another way, segmented regions 282 and 284, when expanded to a given inflation volume, have a diameter less than a sphere expanded to an equal inflation volume.

While expanding in the region between D7 and D8, the structure 280, when inside bone, assumes an increasingly larger surface area and volume, thereby compacting surrounding cancellous bone. Inflation in cancellous bone may occur at the same threshold pressure P(t) as outside bone. However, an increase in the threshold pressure P(t) inside bone is typically required, due to the density of the cancellous bone and resistance of the cancellous bone to compaction.

B. Assembly of an Expandable Balloon Device with an Internal Membrane

FIGS. 23 and 24A-24C depict cross-sectional views of another alternate embodiment of a cavity-forming device constructed in accordance with the teachings of the present invention. Because many of the features of this embodiment are similar to those described in connection with the previous embodiment, like reference numerals will be used to describe similar components.

In this embodiment the cavity-forming device incorporates a balloon 300 comprising a section of dual lumen tubing having an outer wall 310 and an internal membrane 320. The balloon 300 will desirably comprises a material that is commonly used for balloon catheters including, but not limited to, polyethylene, mylar, rubber or polyurethane. Even more desirably, the balloon 300 will comprise an elastomer material, which also possess the capability of being preformed, i.e., to acquire a desired shape by exposure, e.g., to heat and pressure, e.g., through the use of conventional thermoforming, blow molding and/or dip coating techniques. Candidate materials that meet this criteria include polyurethane, silicone, thermoplastic rubber, nylon, and thermoplastic elastomer materials.

In the illustrated embodiment, the balloon 300 comprises plastic material. This material can be processed and extruded in a tubular shape, which can then be cut into individual lengths for further processing. The balloon 300 can be formed by exposing a cut tube length to heat and then enclosing the heated tube within a mold while positive interior pressure is applied to the tube length. For example, one embodiment of a balloon can be formed by heating a length of extruded tubing (incorporating an internal membrane) to 320° F. for approximately 220 seconds, and then stretching the tubing by 10 mm while the tubing is blown at 100 psi in a mold for 45 seconds. The mold can, of course, be part of a conventional balloon forming machine.

In the present embodiment, after the balloon is formed the proximal end 330 of the balloon 300 can be attached to the distal end of an outer catheter body 250 and the distal end 286 of the balloon 300 can be attached to the distal end of an inner catheter body 258. The outer and inner catheters may each comprise extruded tubing made, e.g., from various grades of plastic material, and each can extruded in a tubular shape using, e.g., a screw type extrusion machine.

In assembling the cavity-forming device, the proximal end 330 of the balloon 300 is desirably bonded to the distal end of an outer catheter body 250. In one preferred embodiment (shown in FIGS. 26A-C), a razor blade or other cutting instrument can be used to split approximately 5 mm of the distal end of the outer catheter body, creating a pair of slots 360 (the slot depth is indicated as "A" in FIG. 26B). The proximal end 330 of the dual lumen tubing can then be slid over the distal end of the outer catheter 250, with the outer wall 310 positioned around the distal tip of the outer catheter 250 and the internal membrane positioned within the slots 360. To maintain the flow channels (for the inflation fluid) through the outer catheter tube and into the balloon, a pair of mandrels or inserts (not shown) can be introduced into the outer catheter and balloon in a manner well known in the art. The outer catheter and balloon can then be bonded together using various means including heat bonding, adhesives, or the like. After the bond is formed, the mandrels are removed. Desirably, the splitting of the inner catheter body increases the mechanical strength of the bond between the catheter and tubing and permits the balloon to be more securely bonded to the outer catheter tubing, thereby reducing the opportunity for a proximal bond failure of the balloon.

The distal end 286 of the balloon is also desirably bonded to the distal end of an inner catheter body 258. If desired, the distal end of the inner catheter body 258 may be split and subsequently bonded to the balloon in a similar manner to increase the mechanical strength of the distal bond. Desirably, the inner catheter body will extend through the outer catheter and the balloon.

Figure 26A:
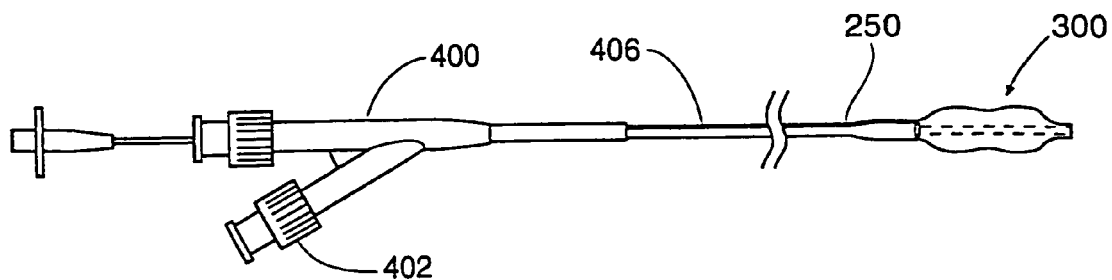
FIGS. 26A-C are perspective views of another alternative embodiment of the expandable structure of FIG. 23.
Figure 26B:
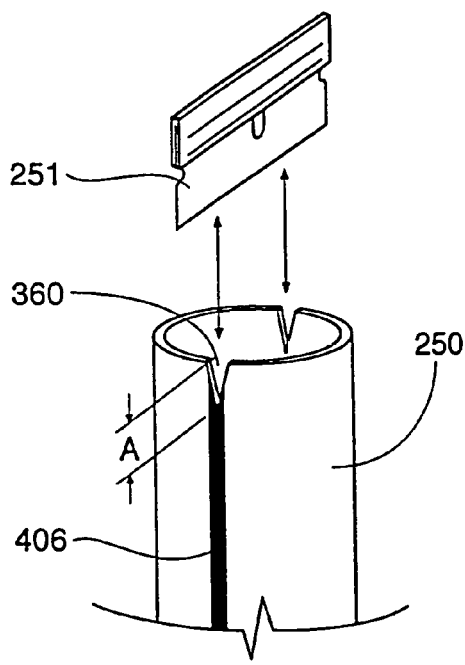
Figure 26C:
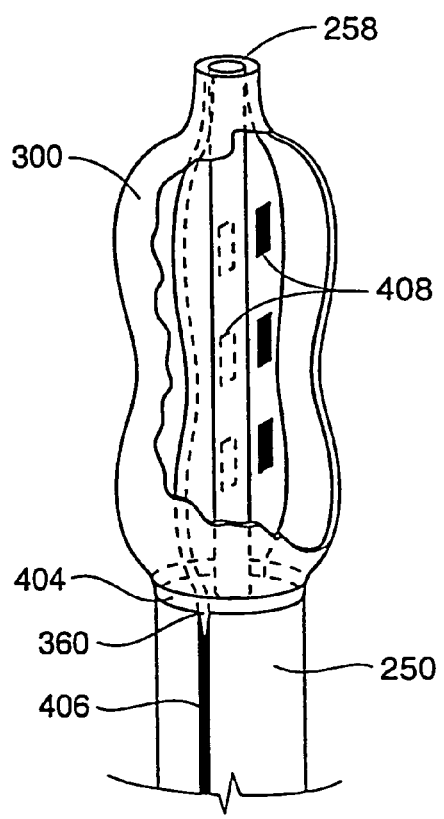

The proximal end of the outer catheter body can be secured to a distal end of a y-shaped luer fitting 400 (see FIG. 26A). The inner catheter body desirably extends through an inner lumen of the luer fitting, and may be bonded to a proximal end of the fitting. Desirably, an inflation fitting 402 of the y-shaped luer fitting will be in fluid communication with the lumen formed between the inner and outer catheters, which will in turn be in fluid communication with the interior of the balloon, such that an inflation fluid introduced into the inflation fitting will inflate the balloon.

Desirably, the outer catheter body and/or y-shaped luer fitting will incorporate a marker (not shown) or other externally viewable indicia which shows a physician the orientation of the internal membrane 320 when the balloon is in a desired position within the patient. Such indicia could include colored markers, indentations and/or protrusions on the outer catheter shaft or y-shaped luer fitting as well as the orientation of the luer fitting itself. By utilizing such indicia, the physician can easily rotate the balloon to a desired orientation within the vertebral body. Because the materials used in constructing medical balloons are typically radiolucent, without such markers it would typically be difficult to gage the orientation of the internal membrane 320 once the catheter is in position within the targeted bone. Alternatively, the internal membrane 320 could incorporate one or more marker bands or other radiopaque substances to depict the orientation of the membrane within the targeted vertebral body.

Various materials can be selected for the component parts of the cavity-forming device. Furthermore, the dimensions of the component parts of the cavity-forming device can also vary, according to its intended use. It should also be understood that, while one described embodiment incorporates dual lumen tubing, various other embodiments could incorporate other types of multi-lumen tubing (including, but not limited to triple, quadruple, etc., lumen tubing), as well as could incorporate membrane(s) having varying orientations and/or positions within the tubing (e.g., symmetrical or asymmetrical).

C. Exemplary Performance Features of the Expandable Structure

Figures 24A, 24B, 24C:
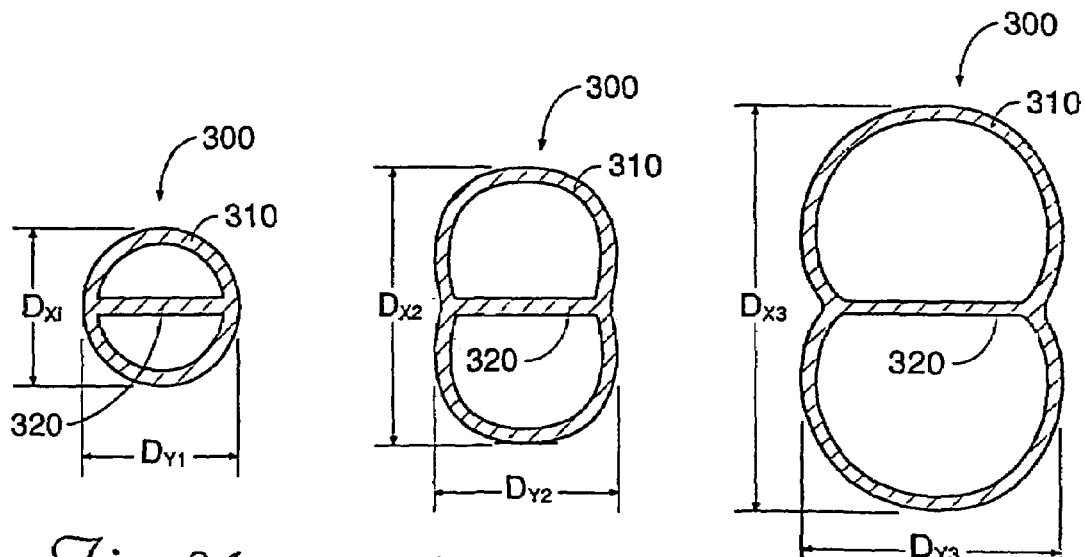
FIGS. 24A-C are cross-sectional views, taken along line 24ABC, of the expandable structure of FIG. 23 undergoing expansion in air.

FIGS. 24A, 24B and 24C show cross-sectional views of the previously-described embodiment of a balloon 300 during its deployment in air. Desirably, the balloon 300 will expand in a similar fashion within the targeted bone such as a vertebral body.

FIG. 24A depicts a cross-sectional view of the balloon 300 when filled with a small amount of inflation fluid, such that the balloon desirably assumes the approximate size and shape of the mold in which the balloon was previously formed, with minimal stresses experienced by the internal membrane 320. In this condition, the expansion of the balloon is substantially circular in cross-section. Accordingly, the vertical and horizontal dimensions of the cross-section of the expanded balloon 300 approximate the dimensions to which the balloon was formed, which in this case are approximately equal, or $D_{X1}=D_{Y1}$.

FIG. 24B depicts the balloon 300 of FIG. 24A when further filled with a pressurized inflation fluid. In this figure, the balloon 300 has assumed a further distended shape, with the wall material of the balloon 300 typically undergoing elastic and/or plastic deformation to assume this enlarged geometry. The balloon desirably does not assume a completely circular cross-sectional shape, principally because the internal membrane resists lateral expansion of the outer walls 310. While some elongation of the internal membrane typically occurs (due to elastic and/or plastic deformation of the membrane itself), the resulting cross-sectional shape is generally ovoid or somewhat similar to a figure-8. In this example the balloon 300, however, is not as significantly restrained from growing in the vertical direction. This combination of restraints results in a balloon which substantially expands or grows more in the vertical direction than in the horizontal direction. Accordingly, the vertical dimension of the expanded balloon 300 is larger than the horizontal dimension of the balloon 300, or $D_{X2}>D_{Y2}$.

FIG. 24C depicts the balloon 300 of FIGS. 24A and 24B when further filled with a pressurized inflation fluid. In this figure, the balloon 300 has assumed an even more distended shape, with the wall material typically having undergone both elastic and significant plastic deformation in order to assume this enlarged geometry. At this point, the balloon is clearly in a non-circular shape, with the internal membrane significantly resisting lateral growth of the balloon (although some additional elastic stretching and/or plastic deformation of the membrane has likely occurred). Accordingly, the vertical dimension of the expanded balloon 300 is significantly larger than the horizontal dimension of the balloon 300, or $D_{X3}>>D_{Y3}$.

For the above-described embodiment, an experimental inflation of the balloon with inflation fluid with volumes of 0 cc to 2 cc and 2 cc to 4 cc produced the following results:

0 cc:
  Balloon Minor diameter (DX1–width): 7.7 mm
  Balloon Major diameter (DY1–height): 7.7 mm
Inflation to 2 cc (Fluid):
  Balloon Minor diameter (DX2–width): 9.2 mm
  Increase in minor (horizontal) diameter: 1.5 mm (width)–[19.5% total increase]
  Balloon Major diameter ($D_{Y2}$–height): 10.9 mm
  Increase in major (vertical) diameter: 2.2 mm (height)–[28.6% total increase]
Inflation to 4 cc (Fluid):
  Balloon Minor diameter ($D_{X3}$–width): 12.7 mm
  Increase in minor (horizontal) diameter: 5 mm (width)–[65% total increase]
  Balloon Major diameter ($D_{Y3}$–height): 15.4 mm
  Increase in major (vertical) diameter: 7.7 mm (height)–[100% total increase]

In addition to axial growth of the balloon as the balloon expands (as previously described), the longitudinal length of a balloon also tends to increase during inflation. This is because the stresses experienced by the balloon material are typically acting in more than one dimension (resulting in material deformation along more than a single axis), causing the overall longitudinal length of the balloon to expand in response to the increased internal pressure. In the present embodiment, however, the internal membrane also tends to reduce the longitudinal growth of the balloon during inflation. For example, for the previously described embodiment of a balloon, a volumetric increase from 2 cc to 4 cc results in a longitudinal length increase for the balloon of only 27.1%. For a similarly constructed balloon that does not incorporate an interior membrane, a volumetric increase from 2 cc to 4 cc results in a longitudinal length increase of 37.1%. Accordingly, the interior membrane of the present invention restrains not only certain aspects of circumferential expansion, but also restrains aspects of longitudinal expansion as well.

The internal membrane of the present embodiment also significantly reduces the opportunity for the balloon to experience a complete radial failure and/or fragment within the patient. During a surgical procedure, if the balloon is punctured or torn, the balloon failure may propagate through a significant amount of the balloon material. If this failure propagates around the entire radius of the balloon, then the distal section of the balloon is in danger of becoming completely separated from the proximal end of the balloon, with only the inner catheter tubing connecting the distal section of the balloon to the cavity-forming device. In such a case, upon removal of the cavity forming device from the patient, it is possible for the inner catheter tubing to fail, leaving the distal section and any balloon fragments in the patient.

The internal membrane of the present embodiment desirably reduces any opportunity for a complete radial failure of the balloon, and also significantly reduces the opportunity for balloon fragments to separate from the cavity-forming device. Where the interior membrane joins the expandable wall, the geometry and/or additional thickness of balloon material at this junction significantly increases the balloon's resistance to failure at his location. A failure which propagates towards such a junction will typically be redirected by the junction—typically the failure will either terminate, will rebound from the junction, and/or will be redirected along the junction.

In the disclosed embodiment, a radial failure which propagates towards the junction will generally be redirected towards the longitudinal axis of the balloon. Moreover, the interior membrane serves to connect the proximal and distal ends of the balloon, which will reinforce the inner catheter tubing in the unlikely event of a complete radial failure of the balloon. Accordingly, because the present embodiment incorporates at least two longitudinally extending junctions, a failure of this embodiment is unlikely to result in a complete radial tear of the balloon material and/or fragmentation of the cavity forming device.

It should also be understood that the direction of expansion of the balloons described herein could similarly be biased towards horizontal inflation, as well as any other angle or orientation desired by the medical practitioner.

D. Assembly of an Expandable Balloon Device with a Longitudinal Bias

FIGS. 29 through 35 depict views of an alternate embodiment of a cavity-forming device constructed in accordance with the teachings of the present invention. Because many of the features of this embodiment are similar to those described in connection with the previous embodiments, like reference numerals will be used to describe similar components.

Figure 29:
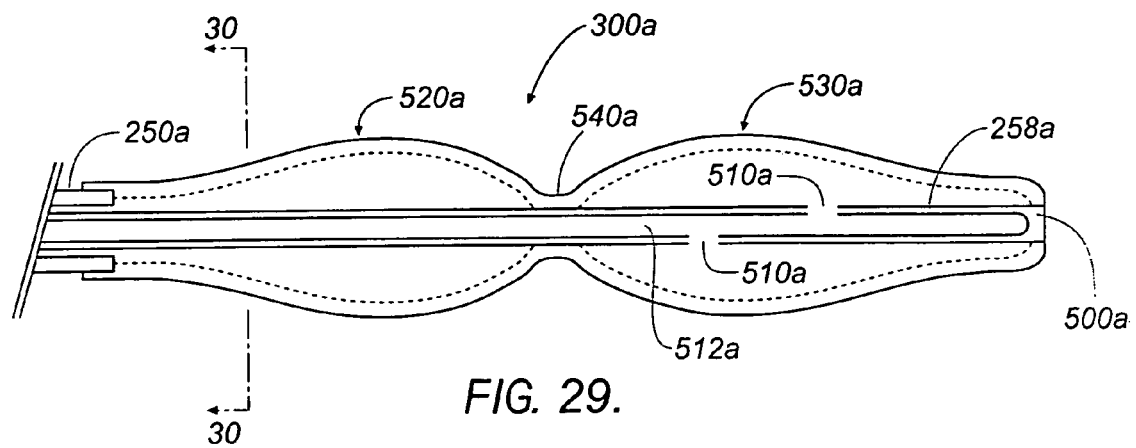
FIG. 29 is a cross-sectional view of an expandable structure incorporating an expansion restraint which facilitates longitudinally biased inflation.
Figure 30:
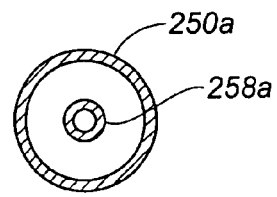
FIG. 30 is a sectional view of the structure of FIG. 29 taken along line 30-30.

In the embodiment shown in FIG. 29, the cavity-forming device incorporates a balloon 300a comprising a section of tubing having an outer wall. The balloon 300a will desirably comprises a material that is commonly used for balloon catheters including, but not limited to, polyethylene, mylar, rubber or polyurethane. Even more desirably, the balloon 300a will comprise an elastomer material, which also possess the capability of being preformed, i.e., to acquire a desired shape by exposure, e.g., to heat and pressure, e.g., through the use of conventional thermoforming, blow molding and/or dip coating techniques. Candidate materials that meet the criteria include polyurethane, silicone, thermoplastic rubber, nylon, and thermoplastic elastomer materials.

In the illustrated embodiment, the balloon 300a comprises plastic material. This material can be processed and extruded in a tubular shape, which can then be cut into individual lengths for further processing. The balloon 300a can be formed by exposing a cut tube length to heat and then enclosing the heated tube within a mold while positive interior pressure is applied to the tube length. The mold can, of course, be part of a conventional balloon forming machine.

In the present embodiment, after the balloon is formed the proximal end of the balloon 300a can be attached to the distal end of an outer catheter body 250a and the distal end of the balloon 300a can be attached to the distal end of an inner catheter body 258a. The outer and inner catheters may each comprise various flexible materials, including medical grade plastic materials like vinyl, polyethylenes, ionomer, polyurethane, and polytetrapthalate (PET) as well as less flexible materials such as Kevlar™, PEBAX®, stainless steel, nickel-titanium alloys, and other metals and/or ceramics. In the present embodiment, the inner and outer catheters each comprise extruded tubing made, e.g., from various grades of plastic material, and each can be extruded in a tubular shape using, e.g., a screw type extrusion machine.

In assembling the cavity-forming device, the proximal end of the balloon 300a is desirably bonded to the distal end of an outer catheter body 250a. In one preferred embodiment, the proximal end of the balloon 300a can be slid over the distal end of the outer catheter 250a. To maintain the flow channel (for the inflation fluid) through the outer catheter tube and into the balloon, one or more mandrels or inserts (not shown) can be introduced into the outer catheter and balloon in a manner well known in the art. The outer catheter 250a and balloon 300a can then be bonded together using various means including heat bonding, adhesives, or the like. After the bond is formed, the mandrel(s) can be removed. The distal end of the balloon is also bonded to the distal end of an inner catheter body 258a. Desirably, the inner catheter body 258a will extend through the outer catheter 250a and the balloon 300a.

If desired, a stiffening stylet (not shown) can extend longitudinally within the inner catheter body 258a to stiffen the cavity-forming device and facilitate its insertion through the cannula. Desirably, the stiffening stylet will increase the stiffness of the catheter to allow the catheter to "push" or impel the balloon through the cannula and into the targeted vertebral body. Desirably, the catheter will be stiff enough to resist an insertion force of more than 100 grams without buckling. Even more desirably, the catheter will be stiff enough to resist an insertion force of more than 200 grams without buckling. Even more desirably, the catheter will be stiff enough to resist an insertion force of more than 300 grams without buckling. Most desirably, the catheter will be stiff enough to resist an insertion force of more than 400, 500 or 1,000 grams without buckling. Desirably, the stiffening stylet will be removable after the cavity-forming device has been inserted or is significantly smaller in diameter than the inner lumen 512a of the inner member 258a, thereby permitting the free flow of inflation fluid through the inner lumen 512a. In one embodiment, the stiffening stylet can be removed after the cavity-forming device has been inserted. Upon removal of this stiffening stylet, the catheter will desirably flex or "droop" a significant amount, thereby allowing the visualization apparatus (such as a C-Arm) to be positioned adjacent the patient without contacting the catheter.

The balloon 300a further incorporates an intermediate or waist section 540a which divides the balloon 300a into at least a proximal lobe 520a and a distal lobe 530a. Desirably, the waist section 540a separates the proximal lobe 520a and the distal lobe 530a of the balloon 300a, such that fluid introduced into one lobe will not flow directly from one lobe into the other. This arrangement desirably permits the lobes to be inflated to and maintained at different internal pressures. If desired, the waist section 540a can be formed by heat bonding or welding a portion of the balloon 300a to the inner catheter body 258 using heated air, heated dies and/or laser or RF energy, or the like. Of course, during the bonding process a mandrel or insert can be used to maintain the flow channel for the inflation fluid.

The distal tip 500a of the inner catheter is desirably closed by heat bonding, adhesives or the like. One or more skives or openings 510a are desirably formed in the wall of the inner catheter 258a to permit fluid communication between the inner lumen 512a of the inner catheter 258a and the interior of the distal lumen 530a of the balloon 300a.

Figure 34:
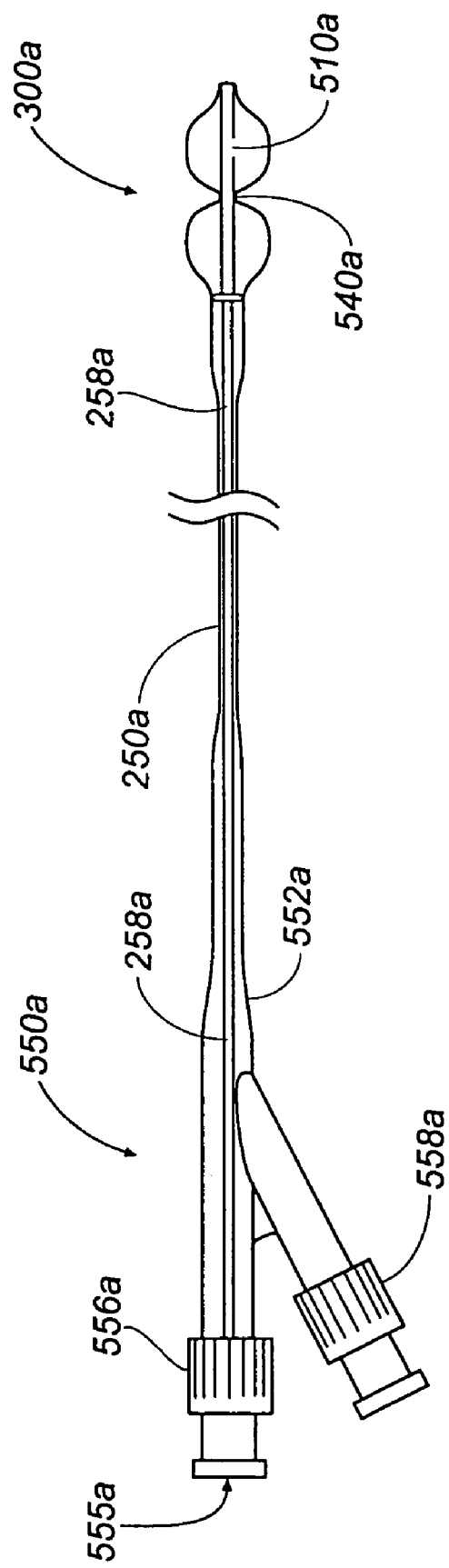
FIG. 34 is a perspective view of a cavity-forming device incorporating the expandable structure of FIG. 29.

As best seen in FIG. 34, the proximal end of the outer catheter body 250a can be secured to a distal end 552a of a y-shaped luer fitting 550a. The inner catheter body 258a desirably extends through an inner lumen of the luer fitting 550a, and can be bonded to a proximal end 555a of the fitting. Desirably, a first inflation fitting 558a of the luer fitting 550a will be in fluid communication with the lumen formed between the inner catheter 258a and outer catheter 250a, which will in turn be in fluid communication with the interior of the proximal lobe 520a of the balloon 300a, such that an inflation fluid introduced into the first inflation fitting 558a will inflate the proximal lobe 520a of the balloon 300a. Desirably, a second inflation fitting 556a of the luer fitting 550a will be in fluid communication with the lumen 512a within the inner catheter 258a, which will in turn be in fluid communication with the interior of the distal lobe 530a of the balloon 300a, such that an inflation fluid introduced into the second inflation fitting 556a will inflate the distal lobe 530a of the balloon 300a. Desirably, the first and second inflation fittings 558a and 556a will incorporate a marker (not shown) or other externally viewable indicia which shows a physician how the inflation fittings correspond to the respective lobes of the balloon 330a. Such indicia could include colored markers, indentations, protrusions, written labels and/or inflation fittings of differing designs.

Various materials can be selected for the component parts of the cavity-forming device. Furthermore, the dimensions of the component parts of the cavity-forming device can also vary, according to its intended use. It should also be understood that, while one described embodiment incorporates two lobes in the balloon, various other embodiments could incorporate other types of multi-lobe balloons (including, but not limited to triple, quadruple, etc., lobes) as well as could incorporate waist sections of varying positions relative to the lobes (e.g., symmetrically positioned between lobes of equal sizes and/or shapes or asymmetrically positioned between lobes of differing sizes and/or shapes, or a combination thereof). For example, the teachings of the present invention could be utilized to create an expandable structure comprising four-lobes by combining the bisecting membrane concept of FIG. 23 with the waist concept of FIG. 29. Such a design could permit selective inflation of individual lobes, thereby mimicking, to some meaningful degree, the asymmetric expansion of a cavity-forming device as described in U.S. Pat. No. 5,972,015, the disclosure of which is incorporated herein by reference. The teachings of the present invention could also be applied where the lobes of the balloons do not extend along the longitudinal axis of the catheter (i.e., where the balloons are "stacked" or "off-axis" from the longitudinal axis of the catheter).

E. Exemplary Performance Features of the Longitudinally-Biased Expandable Balloon Cancellous bone, and to some extent cortical bone, within the bones of a healthy human or animal body will often significantly vary in density, even within the environs of a single bone. In individuals suffering from the effects of diseases and/or drugs that affect bone quality, the local density variations in cancellous bone quality in a single bone may be even more significant. In addition, where surrounding cortical bone has been weakened and/or fractured, this cortical bone may further resist (in varying amounts) attempts at reduction due to the fractured/weakened nature of the cortical bone as well as any subsequent healing of the cortical and/or cancellous bone which may have occurred between the injury and the subsequent treatment.

Where an expandable structure such as a balloon is introduced into a bone, and subsequently enlarged, the density variations and resistance to bone movement of such an environment may cause the balloon to expand in undesirable directions. For example, in a collapsed vertebral body, the outer cortical bone will often be compressed and/or fractured into a wedge-shape, with the anterior portions of the vertebral body more collapsed than the posterior portions of the vertebral body. In such a case, it is typically desired to restore the anatomy of the wedge-shaped vertebral body to its pre-collapsed position. However, the anterior portion of the vertebral body can often strongly resist attempts at reduction, which may be due (at least in part) to the healing of the compressed anterior cortical bone sections as well as the increased density of the cancellous bone in the anterior portion (which can be more compressed than the corresponding cancellous bone in the posterior portion). Expanding an inflatable device in such an environment may cause the device to assume a pyriform or pear-shape, with the most significant increase in device size occurring within the posterior section.

In such a situation, the inflation of the device would desirably be biased towards the anterior section of the vertebral body, with the inflatable device reducing the anterior and posterior sections of the vertebral body by an equivalent amount. More desirably, the device would assume a pyriform or pear-shape with the most significant increase in device size occurring within the anterior section, thereby reducing the fracture to a prefractured anatomical position.

Alternatively, the cancellous bone within the posterior portions of the vertebral body will occasionally be denser than the cancellous bone in the anterior portions (or the posterior cortical bone will be more resistant to reduction, or both), causing the inflatable device to expand significantly more within the anterior portions of the bone. In such a case, it would be desirable to increase the pressure in and/or size of the inflatable device located within the posterior portion of the bone (and possibly compress additional cancellous bone and/or reduce the fracture in the posterior portion) without causing a commensurate increase in the pressure/size of the portion of the inflatable device within the anterior portion of the bone.

Moreover, it may be clinically desirable to continue expanding a portion of an inflatable device, even after another section of the inflatable device has reach a potential clinical endpoint such as, for example, direct contact with cortical bone or balloon puncture and/or failure. By enabling selective inflation of discrete sections of the inflatable device, the disclosed embodiments permit a physician to maximize the reduction and/or augmentation of targeted bones having significant internal density variations.

Figure 31:
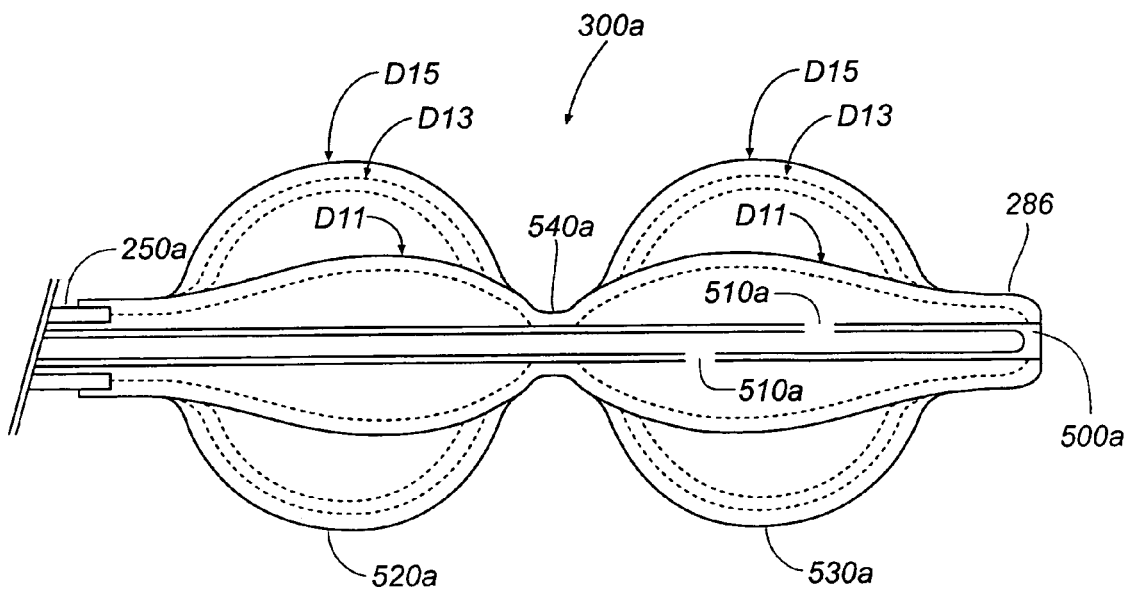
FIGS. 31 through 33 are cross-sectional views of the expandable structure of FIG. 29 undergoing expansion in air.
Figure 32:
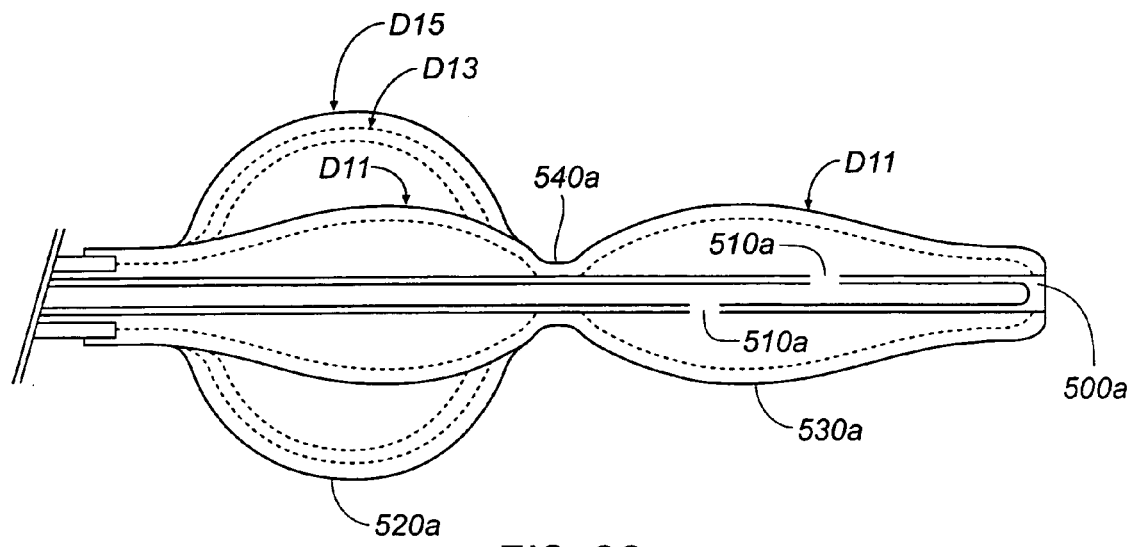
Figure 33:
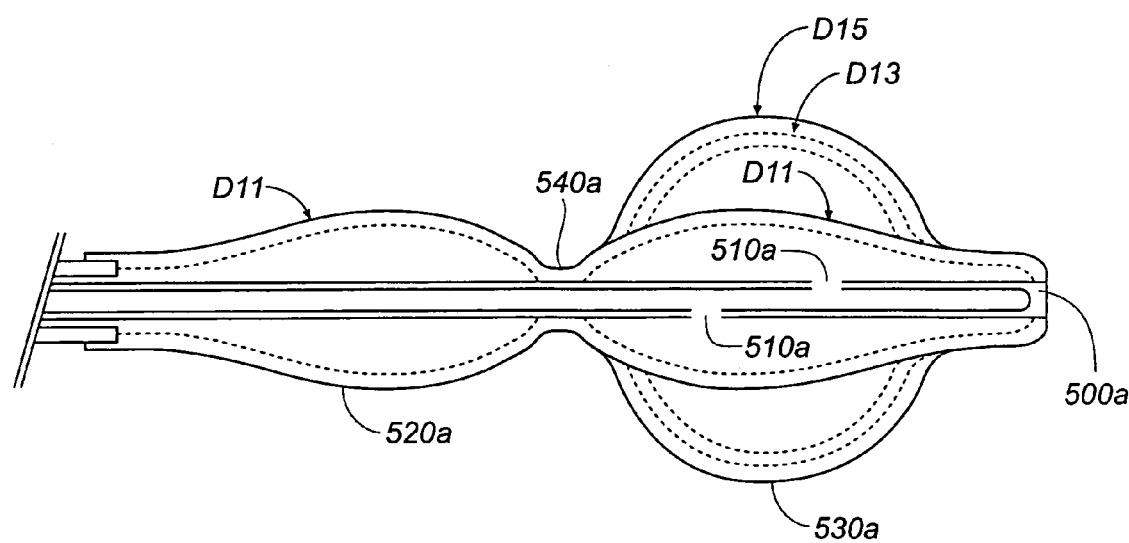

FIGS. 31, 32 and 33 show cross-sectional views of the previously-described embodiment of an expandable structure such as a balloon 300a during its deployment in air. Desirably, the balloon 300a will expand in a similar fashion within the targeted bone such as a vertebral body.

FIG. 31 depicts a cross-sectional view of the balloon 300a when filled with a small amount of inflation fluid such that the balloon 300a desirably assumes the approximate size and shape of the mold in which the balloon was previously formed. The balloon 300a possesses, in an open air environment, a normal non-expanded shape having diameter D11. As the balloon 300a is further filled with a pressurized inflation fluid, the balloon subsequently assumes the expanded shape having a diameter D13 and, after further inflation, ultimately reaches an expanded shape having a diameter D15. During this expansion, the wall material of the balloon 300a will typically be undergoing elastic and/or plastic deformation to assume this enlarged geometry, although various inelastic materials could be used for the wall material of the balloon 300a, if desired.

FIGS. 32 and 33 depict the proximal lobe 520a and the distal lobe 530a of the expandable structure, respectively, being expanded individually. In FIG. 32, inflation fluid is introduced into the lumen between the outer catheter tube 250a and the inner catheter tube 258a where it enters the interior of the proximal lobe 520a of the balloon 300a and expands the proximal lobe 520a. Desirably, such expansion of the proximal lobe 520a will have little or no effect upon the expansion of the distal lobe 530a. Similarly, FIG. 33 depicts the introduction of inflation fluid into the lumen 512a in the inner catheter tube 258, whereby the fluid subsequently passes through one or more skives 510a and into the interior of the distal lobe 530a of the balloon 300a, where it expands the distal lobe 530a. As with the expansion of the proximal lobe 520a, expansion of the distal lobe 530a will desirably have little or no effect upon the expansion of the proximal lobe 520a. In addition, in the disclosed embodiment the waist section 540a will desirably experience little or no increase in diameter as the corresponding lobes increase in diameter, although corresponding waist growth may be desired in other embodiments.

Figure 35:
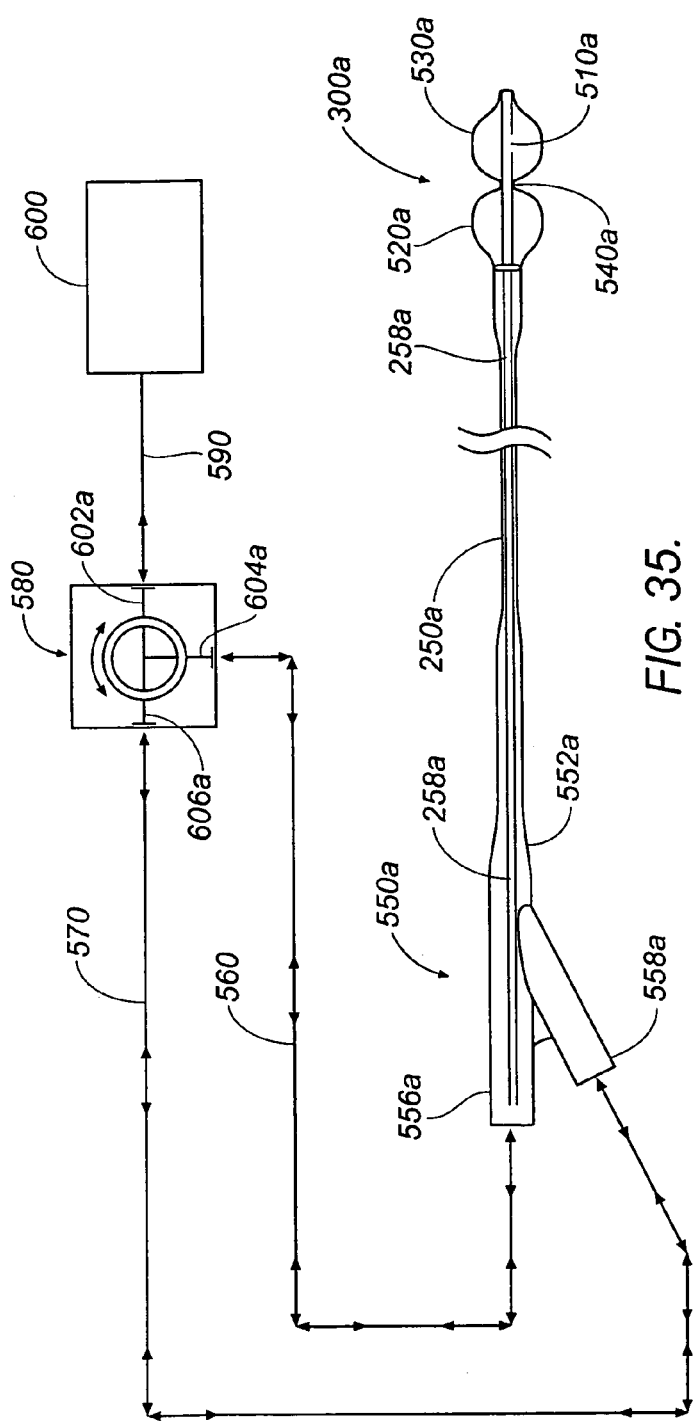
FIG. 35 is a partial schematic view of the cavity-forming device of FIG. 34 with one embodiment of an associated inflation fluid distribution system.

FIG. 35 depicts a partial-schematic view of the expandable structure of FIGS. 29 through 34, with one embodiment of an inflation fluid distribution system. In this distribution system an inflation fluid source 600 is connected through a source line 590 to an input 602a of a three-way valve 580 (such as valve model number 99739—suitably modified to permit 360° rotation of the selector arm—commercially available from Qosina of Edgewood, N.Y.). A first output 606a of the three-way valve 580 is connected through a first line 570 to the first inflation fitting 558a of the luer fitting 550a. A second output 604a of the three-way valve 580 is connected through a second line 560 to the second inflation fitting 556a of the luer fitting 550a. Desirably, inflation fluid passing through the first output 606a will cause inflation and/or deflation of the proximal lobe 520a of the balloon 300a, while inflation fluid passing through the second output 604a will cause inflation and/or deflation of the distal lobe 530a of the balloon 300a. In order to assure that the first and second lines 570 and 560 are connected to the correct valve/fitting combination, various identifiers can be used, including color coding, identification markings, and/or unique valves and/or fittings.

Figure 38:
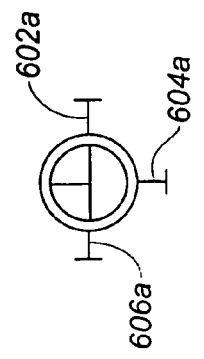
FIGS. 36 through 38 are schematic views showing various orientations of a three-way valve in the fluid distribution system of FIG. 35.
Figure 37:
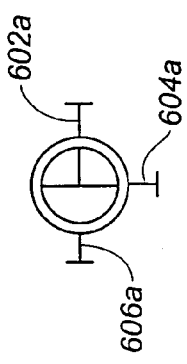
Figure 36:
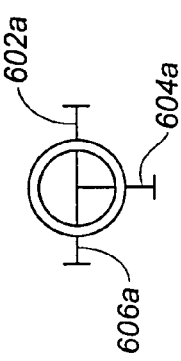

By altering the orientation of the selector of the three-way valve 580, inflation fluid introduced into and/or removed from the system can selectively cause inflation of the proximal lobe, the distal lobe or both lobes simultaneously. For example, FIG. 36 depicts a selector orientation which establishes communication between the inflation fluid source 600 and both lobes, permitting simultaneous inflation or deflation of both lobes of the balloon 300a. FIG. 37 depicts a selector orientation which establishes communication between the inflation fluid source and the distal lobe 530a, permitting inflation or deflation of only the distal lobe 530a. FIG. 38 depicts a selector orientation which establishes communication between the inflation fluid source 600 and the proximal lobe, permitting inflation or deflation of only the proximal lobe 520a. Of course, if desired, the orientation of the selector can be altered at any time during the procedure to permit various combinations of biased inflation, including the partial inflation or deflation of one or more lobes, as desired. Alternatively, multiple sources of inflation fluid could be used to individually expand/contract each lobe. In addition, one or more check valves (not shown) could be incorporated in the distribution system to prevent undesired deflation and/or pressure loss within individual lobes due to factors such as lobe failure, etc.

In the case of a collapsed vertebral body where the outer cortical bone has compressed and/or fractured into a wedge-shape (with the anterior portion of the vertebral body more collapsed than the posterior portion of the vertebral body), the present expandable structure can be introduced into the vertebral body in the previously-taught manner, and expanded. If the anterior portion of the vertebral body strongly resists attempts at reduction, causing the inflatable device to assume a pyriform or pear-shape (biased towards the proximal portion of the bone), the three-way valve can be repositioned to direct inflation fluid towards the distal lobe, thereby increasing the volume and/or pressure of the distal lobe in a desired manner to obtain the desired reduction of the fracture. After sufficient inflation fluid has been introduced into the distal lobe, the three-way valve can be repositioned (if desired) to continue the procedure, and these steps can be repeated as necessary. Once the targeted bone has been reduced, or another clinical endpoint has been reached, the inflatable device can remain within the patient (to permit healing of the fracture) or can be removed and replaced with a bone filling material.

III. Implant Creation and Performance

Once the balloon 300 is in a desired position within a targeted bone (in this example a vertebral body), an inflation medium can be introduced into the balloon, which desirably expands the balloon within the targeted bone. The balloon will desirably assume a similar shape within the targeted bone as it would in air, thereby creating a cavity within the bone that is substantially the same shape and size as the inflated balloon. It must be understood, however, that variations in cancellous bone density and quality may distort the final expanded size and shape of the inflated balloon, such that the expanded balloon is significantly different in size and shape than it would be when expanded in air.

While the restraints described herein may not absolutely guarantee that the final shape and size of the balloon (and thus the cavity) will be identical to the shape and size of the balloon in air, the restraints described herein significantly increase the potential for creating an optimally sized and shaped cavity to achieve one or more desired treatment goals. For example, if the desired treatment goal is the reinforcement and/or repair of a targeted vertebral body, a balloon may be chosen that incorporates restraints to maximize vertical growth of the balloon (in this context, the vertical orientation can be assumed to be parallel to the longitudinal axis of the spine) while minimizing horizontal and/or longitudinal growth of the balloon. If desired, this balloon could also incorporate restraints that reduce, minimize and/or bias balloon expansion along its longitudinal axis.

Alternatively, a physician may desire a balloon that incorporates restraints to maximize horizontal growth of the balloon (in this embodiment, horizontal growth can be assumed to be transverse to the longitudinal axis of the spine) while minimizing vertical growth of the balloon. Such a balloon (which could simply be the previously described embodiment when rotated 90° about its longitudinal axis) could be used to initially create a cavity extending across substantially the entire vertebral body. After removal of the first balloon, a second balloon (of the same or different design) could subsequently be introduced into the horizontal cavity and expanded. If desired, the second balloon could substantially fill the horizontal cavity prior to inflation (thereby maximizing the surface area of the balloon facing the upper and lower endplates) and, when expanded, could maximize the vertical forces which ultimately act on the endplates of the vertebral body (in an attempt to displace the surrounding cortical bone).

If desired, a balloon chosen for treatment of a vertebral body may further incorporate restraints that cause the balloon to expand into an irregular shape. In one embodiment disclosed herein, best shown in FIG. 23, the balloon desirably expands to a "peanut-like" shape when viewed from the side. This embodiment will desirably create a cavity that is similarly "peanut-shaped", with the cavity essentially comprising a pair of enlarged cavity lobes that are separated by a region of reduced cavity size—in other words, the cavity is dumb-bell shaped. Desirably, the filler material which occupies this cavity will harden, set and/or solidify into an implant having substantially the shape of the cavity into which it was introduced. By forming the implant into this dumb-bell shape, the region of reduced width of the implant will desirably help to anchor the implant within the cancellous bone, thereby reducing the opportunity for the implant to displace along the longitudinal axis of the implant and/or migrate within or outside the treated bone. Moreover, in the embodiment disclosed in FIGS. 29-35, the waist region, which typically expands less that the surrounding lobes, will create a cavity having an even-more exaggerated "peanut-shape", further anchoring the implant placed therein.

Furthermore, if desired a balloon used for treatment of a vertebral body could incorporate additional restraints that alter the outer shape of the expanded balloon to further reduce the opportunity and/or tendency of an implant to migrate within and/or outside of a treated bone. For example, in one embodiment described above, the balloon incorporates an internal membrane which desirably causes the expanded balloon to assume an indented or elongated "figure-8" shape in cross-section (see FIG. 24c). This shape, if formed into the cavity walls and ultimately assumed by the filler material, will desirably create an implant of similar cross-section. By forming the implant into this figure-8 shape, the implant will desirably be anchored within the cancellous bone, thereby reducing the opportunity for the implant to rotate about the longitudinal axis of the implant and/or migrate within or outside the treated bone.

In addition to creating a desired shape and size to the cavity, which will desirably act as a mold to bound and shape the filler material, the physician can further customize the shape of the implant in various ways. For example, after the initial cavity formation, but prior to the introduction of the filler material, the physician could use other surgical instruments to alter the shape and/or size of the cavity, such as by removing additional cancellous bone and/or scoring the compressed cancellous bone along the walls of the cavity. Similarly, prior to introducing the filler material the physician could introduce one or more additional balloons into the cavity to alter the existing cavity dimensions and/or create additional cavities of unique and/or desired shape. The physician could alternatively choose to introduce two or more different bone filler materials into a single cavity, with different materials occupying different portions of the cavity and/or being intertwined, mixed or separated in some manner, if desired. In addition, after the filler material has filled the entire cavity, the physician could continue introducing an additional amount of bone filler material, which would desirably cause small amounts of the bone filler material to interdigitate or flow into various gaps and/or cracks in the walls of the cavity, thereby further anchoring the resulting implant within the cancellous bone. For example, the injection of an additional ½ cc, 1 cc or 1 cc of bone filler material (beyond the volume of the cavity created within the cancellous bone) can significantly increase the interdigitation of bone filler material with the surrounding cancellous bone matrix.

IV. Other Uses, Methods and Balloons

The cavity created by the balloon can be filled with a medically-appropriate formulation of a drug or a growth factor. As an example of delivering a drug, a typical dose of the antibiotic, gentamicin, to treat a local osteomyelitis (bone infection), is 1 gram (although the therapeutic range for gentamicin can be far greater, from 1 nanogram to 100 grams, depending on the condition being treated and the size of the area to be covered). A medically-suitable gel formulated with appropriate gel materials, such a polyethylene glycol, can contain 1 gram of gentamicin in a set volume of gel, such as 10 cc. A balloon with this volume whose shape and size is appropriate for the site being treated (that is, the balloon desirably will not break the cortical bone when inflated at the chosen site) can be used to compact the infected cancellous bone. This creates a space that can be filled with the antibiotic gel in an open or minimally invasive procedure. This places and holds the required amount of drug right at the site needing treatment, and protects the drug from being quickly washed away by blood or other fluids. Not only can the dose be optimized, but additional doses can be applied at later times without open surgery, enhancing the therapeutic outcome. If the required cavity for the optimal drug dose weakens the bone, the bone can be protected from future fractures with a cast or with current internal or external metal or plastic fixation devices. The therapeutic substance put into bone may be acting outside the bone as well. A formulation containing chemotherapeutic agent could be used to treat local solid osteosarcoma or other tumor near that bone.

As an alternative, to deliver therapeutic substances, balloons can be dipped in a medical formulation (often a dry powder, liquid or gel) containing a medically-effective amount of any desired antibiotic, bone growth factor or other therapeutic agent to coat the balloon with the above-mentioned substance before it is inserted into a bone being treated. Optionally, the balloon can be wholly or partially inflated with air or liquid before the coating is performed. Optionally, the coated balloon can be dried with air or by other means when the applied formulation is wet, such as a liquid or a gel. The balloon is refolded as required and either used immediately or stored, if appropriate and desired. Coated on the balloon, therapeutic substances can be delivered while cancellous bone is being compressed, or with an additional balloon once the cavity is made.

The methods described above can also be used to coat Gelfoam® absorbable gelatin powder or other agents onto the balloon before use. Such agents may also comprise substances that desirably promote coagulation and/or thickening of body fluids. Inflating a Gelfoam-coated balloon inside bone may further fill any cracks in fractured bone not already filled by the compressed cancellous bone.

FIGS. 22A-C schematically illustrate one system and method for delivering a therapeutic substance to the bone according to the present invention. As shown in FIG. 22A, an inflated balloon 229 attached to an inflating tube 230 is stabilized with a clip 231 that couples tube 230 to a wire 232. As shown in FIG. 22B, a measured amount of gel formulation containing the desired amount of substance 233 is uniformly dispensed from a container 234, preferably in thin lines 235, onto the outer surface of a balloon 236. As shown in FIG. 22C, the coated balloon 23 is then deflated and allowed to dry until the gel sets. The coated balloon 237 is then ready for packaging for use by the surgeon. Of course, the balloon can also be coated without prior inflation. In addition, the coating substance can be the desired compound alone in its natural state (solid, liquid or gas) or in an appropriate formulation, for example, a dry powder, an aerosol or a solution. The optional drying time will, of course, depend on the nature of the compound and its formulation.

Delivering a therapeutic substance on the outside of the balloon used to compact the bone or with a second (possibly slightly larger) balloon after the bone is compacted, is qualitatively different than putting formulated drug into the cavity. When delivered while compressing the bone, the substance becomes incorporated into the compacted bone. This can serve as a way to instantly formulate a slow release version of the substance. It simultaneously allows the surgeon to fill the cavity with an appropriate supporting material, like acrylic bone cement or biocompatible bone substitute, so no casting or metal fixation is required. Such a combination allows the surgeon, for example, to percutaneously fix an osteoporotic fracture while delivering a desired therapeutic substance (like an antibiotic, bone growth factor or osteoporosis drug) to the site. Thus, casts or metal fixation devices may not be required in such instances.

Medically-effective amounts of therapeutic substances are typically defined by their manufacturers or sponsors and are generally in the range of 10 nanograms to 50 milligrams per site, although more or less may be required in a specific case. Typical antibiotics include gentamicin and tobramycin.

Typical bone growth factors are members of the bone morphogenetic factor, osteogenic protein, fibroblast growth factor, insulin-like growth factor, and transforming growth factor alpha and beta families. Chemotherapeutic and related agents include compounds such as cisplatin, doxorubicin, daunorubicin, methotrexate, taxol and tamoxifen. Osteoporosis drugs include estrogen, calcitonin, diphosphonates, and parathyroid hormone antagonists.

The balloons described in this invention can be used in open surgical procedures at the sites discussed above to provide an improved space for inserting orthopedic implants, bone graft, bone substitutes, bone fillers or therapeutic substances. The size and shape of balloon chosen will be determined depending upon the site being treated as well as the size, shape or amount of material that the surgeon wants to insert into the remaining bone. Square and rectangular balloons can be used at any site for the placement of bone substitutes like hydroxyapatites which are available in those shapes. Balloons would desirably be made to match those predetermined sizes, and the surgeon would chose the balloon to fit the size of material chosen.

To insert materials which do not flow into the balloon-made cavity, like hydroxyapatite granules or bone mineral matrix, the surgeon can push them down a tube with a long pin whose diameter is slightly more narrow than the inner diameter of the cannula through procedures in which the minimally-invasive procedure is taking place. During open surgery, the surgeon can approach the bone to be treated as if the procedure is percutaneous, except that there is no skin and other tissues between the surgeon and the bone being treated. This desirably keeps the cortical bone as intact as possible. If the material to be inserted does not flow and should not be pushed into the cavity through a cannula (as in the case of the hydroxyapatite block, because that may result in significant damage to the patient), the surgeon can make the cavity using the "minimally invasive" approach, then punch a hole using standard tools (such as a punch, gouge or rasp) into one side of the cortical bone to allow insertion of the block. This same approach can be used for implanting a metal prosthesis, such as the metal tibial component of a total knee replacement system.

Different sizes and/or shapes of balloons may be used at sites not specified above, such as the jaw bones, the midshaft of the arm and leg bones, the cervical vertebral bodies, the foot and ankle bones, the ribs and the like. One of the keys to choosing balloon shape and size in treating or preventing bone fracture is the teaching of this application that, optimally, up to 70-90% (or greater) of the cancellous bone can be compacted in cases where the bone disease causing fracture (or the risk of fracture) is the loss of cancellous bone mass (as in osteoporosis). Compacting less than 70-90% of the cancellous bone at the site being treated could possibly leave an extensive amount of the diseased cancellous bone at the treated site. The diseased cancellous bone could remain weak and later collapse, causing fracture despite treatment. With this principle, the allowed shapes and minimum sizes for any chosen bone are explained and defined.

Of course, there are many exceptions to this 70-90% cavity size, as generally described in this specification. One exception is when the bone disease being treated is localized, as in avascular necrosis, where local loss of blood supply is killing bone in a limited area. In that case, the balloons can be smaller, because the disease area requiring treatment is often smaller. A second exception is in the use of the devices to improve insertion of solid materials in defined shapes, like hydroxyapatite and components in total joint replacement. In these cases, the balloon shape and size is generally defined by the shape and size of the material being inserted. Another exception is the delivery of therapeutic substances. In this case, the cancellous bone may or may not be affected. If it is not, some of the cancellous bone can be sacrificed by compacting it to improve the delivery of a drug or growth factor which has an important therapeutic purpose. In this case, the bone with the drug inside is supported while the drug works and then the bone heals through casting or current fixation devices. Another exception can involve the treatment of bone tumors, where the creation of a small cavity in cancellous bone adjacent the tumor could facilitate the minimally invasive manipulation and/or removal of the tumor. Another exception could be where the quality of the cancellous bone is generally good, but the bone has fractured and/or collapsed in some manner. In such a case, the creation of a small cavity within the stronger cancellous bone may displace the cortical bone fragments to a position at or near the fragments' normal anatomic positions without significantly compressing a significant portion and/or all of the cancellous bone.

Another key to choosing balloon shape and size is one teaching of this invention, that inelastic, elastic and/or semi-elastic balloon restraints can be utilized and that inelastic or semi-elastic balloon materials are often preferred. Such materials can safely and easily prevent the balloon from expanding beyond its predetermined shape and size which can be defined by the limits of the normal dimensions of the outside edge of the cancellous bone (which is inside of the cortical bone). A balloon which expands too much, for example, can create the risk of immediate fracture, so in one embodiment this defines the upper limits of balloon sizes at each site. With many typical angioplasty balloons, surgeons usually rely on monitoring pressure (instead of the balloon design features of this invention) to prevent their balloons from inflating too much. This often requires greater surgical skill than the teachings of the present application, which in various embodiments is to take an X-ray of the site to be treated and measure the important dimensions as described herein. In addition, in bone treatment, relying on pressure can often result in an inferior clinical outcome. The surgeon generally will not know in advance what pressure is required to completely compact the cancellous bone, because this varies depending on the thickness of the cancellous bone and the extent to which it has lost density due to its disease. The surgeon is often likely to under inflate the balloon to avoid the potential consequences of overinflation and/or cortical bone fracture.

Another teaching of this application is that, while maximal pressures equally exerted in all directions can typically compress the weakest areas of cancellous bone, the use of restraints in a balloon body will desirably control balloon expansion to some degree. If the balloon design does not incorporate restraints, it may not compress cancellous bone in an optimal manner for reinforcement and/or repair of a fractured vertebral body. The shape of the cancellous bone to be compressed, and the local structures that could be harmed if bone were moved inappropriately, are generally understood by medical professionals using textbooks of human skeletal anatomy along with their knowledge of the site and its disease or injury. Ranges of shapes and dimensions are defined by the site to be treated. Precise dimensions for a given patient can be determined by X-ray of the site to be treated, the therapeutic goal and safety constraints at the site. For diseased bone, replacement of most of the cancellous bone may be desired, so a balloon whose shape and size will compress around 70-90% (or greater) of the volume of the cancellous bone in the treated region can be chosen.

However, as previously noted balloons that are smaller or larger may be appropriate, particularly where localized bone treatments and/or delivery of a therapeutic substance is the main goal. If desired, the balloon size can be chosen by the desired amount of therapeutic substance, keeping in mind that the balloon should desirably not displace the cortical bone beyond its normal unfractured dimensions.

While the new devices and methods have been more specifically described in the context of the treatment of human vertebrae, it should be understood that other human or animal bone types can be treated in the same or equivalent fashion. By way of example, and not by limitation, the present systems and methods could be used in any bone having bone marrow therein, including the radius, the humerus, the vertebrae, the femur, the tibia or the calcaneus. In addition, other embodiments and uses of the invention will be apparent to those skilled in the art from consideration of the specification and practice of the invention disclosed herein. All documents referenced herein are specifically and entirely incorporated by reference. The specification and examples should be considered exemplary only with the true scope and spirit of the invention indicated by the following claims. As will be easily understood by those of ordinary skill in the art, variations and modifications of each of the disclosed embodiments can be easily made within the scope of this invention as defined by the following claims.

What is claimed is:

1. A method comprising
providing a system comprising a void creation device capable of being inserted through a percutaneous access path into a bone having cortical walls which enclose a cancellous bone volume, the void creation device including an expandable structure and including a first expandable region capable of expanding in the cancellous bone volume to compact a first region of the cancellous bone volume to form a first void, and a second expandable region spaced from the first expandable region and capable of expanding in the cancellous bone volume substantially independently of the first expandable region to compact a second region of the cancellous bone volume different than the first region of the cancellous bone volume to form a second void, and an expansion controller coupled to the expandable structure being capable of selective operation in a first condition to expand the first expandable region without substantially expanding the second expandable region and in a second condition to expand the second expandable region without substantially expanding the first expandable region,
inserting the void creation device into a bone through a percutaneous access path, and
operating the expansion controller to form at least one void in cancellous bone within the bone.

2. A method according to claim 1, wherein at least one of the expandable regions includes an internal restraints which allows for directional expansion of the respective expandable region.

3. A method according to claim 1
wherein the expansion controller is further capable of operation in a third condition to expand both the first and second expandable regions substantially simultaneously.

4. A method according to claim 1
wherein the expansion controller is capable of selectively collapsing the first expandable region without substantially collapsing the second expandable region, and vice versa.

5. A method according to claim 1
wherein the expansion controller is capable of selectively collapsing both the first expandable region and the second expandable region substantially simultaneously.

6. A method according to claim 1
wherein the bone comprises a vertebral body.

7. A method according to claim 1
wherein at least one of the first and second expandable regions comprises an inflatable body.

8. A method according to claim 7
wherein the expansion controller includes a valve controlling conveyance of an inflation medium to the inflatable body.

9. A method according to claim 1
wherein the expandable structure is elongated along an axis and includes proximal and distal end spaced apart along the axis, the first expandable region being located near the proximal end and the second expandable region being located near the distal end.

10. A method according to claim 9
wherein the expandable structure includes an intermediate section between the proximal and distal ends that does not significantly expand during expansion of the first and/or second expandable regions.

11. A method according to claim 10
wherein the first and second expandable regions, when substantially expanded, comprise lobes.

12. A method according to claim 1
further including placing a volume of filling material into the void.

13. A method according to claim 12
wherein the filling material hardens within the void.

* * * * *